US007348400B2

(12) United States Patent
Livett et al.

(10) Patent No.: US 7,348,400 B2
(45) Date of Patent: Mar. 25, 2008

(54) α-CONOTOXIN PEPTIDES WITH ANALGESIC PROPERTIES

(75) Inventors: Bruce Grayson Livett, 48 Nicholas Street, Melbournea, Victoria (AU) 3147; Zeinab Khalil, Melbourne (AU); Kenwyn Ronald Gayler, Melbourne (AU); John Geoffrey Down, Melbourne (AU); David William Sandall, Edithvale (AU); David Anthony Keays, Oxford (GB)

(73) Assignee: Bruce Grayson Livett, Melbourne (AU)

( * ) Notice: Subject to any disclaimer, the term of this patent is extended or adjusted under 35 U.S.C. 154(b) by 78 days.

(21) Appl. No.: 10/473,246

(22) PCT Filed: Mar. 28, 2002

(86) PCT No.: PCT/AU02/00411

§ 371 (c)(1),
(2), (4) Date: Aug. 26, 2004

(87) PCT Pub. No.: WO02/079236

PCT Pub. Date: Oct. 10, 2002

(65) Prior Publication Data

US 2005/0215480 A1 Sep. 29, 2005

(30) Foreign Application Priority Data

Mar. 29, 2001 (AU) .................................... PR4094

(51) Int. Cl.
*C07K 7/00* (2006.01)
*C07K 14/435* (2006.01)

(52) U.S. Cl. ...................... 530/326; 530/327; 530/324; 530/855; 514/13; 514/14; 435/7.1; 424/9.1; 536/23.1

(58) Field of Classification Search ................ 530/326, 530/327, 324, 855; 514/13, 14; 435/7.1; 424/9.1; 536/23.1
See application file for complete search history.

(56) References Cited

U.S. PATENT DOCUMENTS

| | | | | |
|---|---|---|---|---|
| 5,514,774 | A | 5/1996 | Olivera et al. | |
| 5,589,340 | A | 12/1996 | Olivera et al. | |
| 5,633,347 | A | 5/1997 | Olivera et al. | |
| 6,797,808 | B1 * | 9/2004 | Watkins et al. | 530/326 |
| 2003/0109670 | A1 * | 6/2003 | Olivera et al. | 430/324 |

FOREIGN PATENT DOCUMENTS

| | | |
|---|---|---|
| WO | WO 95/01436 A | 1/1995 |
| WO | WO 98/51322 A | 11/1998 |
| WO | WO 99/33482 A | 7/1999 |
| WO | WO 00/43409 | 7/2000 |
| WO | WO 00/43409 A | 7/2000 |
| WO | WO 00/44776 A | 8/2000 |
| WO | WO 02/07750 A | 1/2002 |

OTHER PUBLICATIONS

Loughnan M. et al., "α-Conotoxin EpI, a Novel Sulfated Peptide from *Conus episcopatus* That Selectively Targets Neuronal Nicotinic Acetylcholine Receptors", Journal of Biological Chem. (1998), vol. 273, No. 25, p. 25, 15667-15674.
Broxton N. et al., "Leu 10 of α-conotoxin PnIB confers potency for neuronal nicotinic responses in bovine chromaffin cells", European Journal of Pharmacology (2000), vol. 390, No. 3, pp. 229-236.
Quiram P.A. et al. "Pairwise Interactions between Neuronal $\alpha_7$ Acetylcholine Receptors and α-Conotoxin PnIB", Journal of Biological Chemistry (2000), vol. 275, No. 7, pp. 4889-4896.
Luo S. et al., "α-Conotoxin AuIB Selectively Blocks α3β4 Nicotinic Acetylcholine Receptors and Nicotine-Evoked Norepinephrine Release", Journal of Neuroscience (1998), vol. 18, No. 21, pp. 8571-8579.
Fainzilber M. et al, "A New Neurotoxin Receptor Site on Sodium Channels is Identified by a Conotoxin That Affects Sodium Channel Inactivation in Molluses and Acts as an Antagonist in Rat Brain", Journal of Biological Chem. (1994), vol. 269, No. 4, pp. 2574-2580.
Luo S. et al, "Single-Residue Alteration in α-Conotoxin PnIA Switches Its nAChR Subtype Selectivity", Biochemistry (1999), vol. 38, pp. 14542-14548.
Rogers J.P. et al. "NMR Solution Structure of α-Conotoxin ImI and Comparison to Other Conotoxins Specific for Neuronal Nicotinic Acetylcholine Receptors", Biochemistry (1999), vol. 38, pp. 3874-3882.
Database Embl—Cone Snail Alpha-Conotoxin Coding Sequence Seq ID No. 291, Jan. 19, 2001, EBI Database Accession No. AAA89478.
Database Embl—cDNA Encoding Conotoxin Peptide #1 Precursor, Jul. 18, 2000, EBI Database Accession No. AAA10453.
Database Embl.—Conus Textile Alpha A Conotoxin Tx2 Precursor, May 24, 1999, EBI Database Accession No. AF146353.
Robert M. Jones, et al., "Conus Peptides—Combinatorial Chemistry at a Cone Snail's Pace", Current Opinion in Drug Discovery and Development, 2000, vol. 3, No. 2, pp. 141-154.
J. Michael McIntosh, et al., "Conus Peptide Targeted to Specific Nicotinic Acetyllcholine Receptor Subtypes", Annual Review of Biochemistry, 1999, vol. 68, pp. 59-88.

* cited by examiner

*Primary Examiner*—Chih-Min Kam
(74) *Attorney, Agent, or Firm*—Browdy and Neimark, P.L.L.C.

(57) ABSTRACT

This invention relates to novel α-conotoxin-like peptides comprising the following sequence of amino acids: $Xaa_1CCSXaa_2Xaa_3Xaa_4CXaa_5Xaa_6Xaa_7Xaa_8Xaa_9Xaa_{10}$-$Xaa_{11}C$—$NH_2$ in which $Xaa_1$ is G or D; $Xaa_3$ is proline, hydroxyproline or glutamine; each of $Xaa_2$ to $Xaa_8$ and $Xaa_{11}$ is independently any amino acid; $Xaa_9$ is proline, hydroxyproline or glutamine; $Xaa_{10}$ is aspartate, glutamate or γ-carboxyglutamate; $Xaa_{11}$ is optionally absent; and the C-terminus is optionally amidated, with the proviso that the peptide is not α-conotoxin Ep1 or α-conotoxin Im1. The peptides are useful in the treatment or prevention of pain, in recovery from nerve injury, and in the treatment of painful neurological conditions such as stroke.

16 Claims, 18 Drawing Sheets

```
1     ATGGGCATGCGGATGATGTTCACCGTGTTTCTGTTGGTTGTCTTGGCAACCACTGTCGTT   60
       M  G  M  R  M  M  F  T  V  F  L  L  V  V  L  A  T  T  V  V

61    TCCTCCACTTCAGGTCGTCGTGAATTTCGTGGCAGGAATGCCGCAGCCAAAGCGTCTGAC   120
       S  S  T  S  G  R  R  E  F  R  G  R  N  A  A  A  K  A  S  D

121   CTGGTCAGTTTGACCGACAAGAAGCGAGGATGCTGTAGTGATCCTCGCTGTAACTATGAT   180
       L  V  S  L  T  D  K  K  R  G  C  C  S  D  P  R  C  N  Y  D
                                  _____________________________
                                          Toxin Region

181   CATCCAGAAATTTGTGGTTGAAGACGCTGATGCTCCACGACCCTCTGAACCACGACACGC   240
       H  P  E  I  C  G  *
      __________________

241   CGCCCTCTGCCTGACCTGCTTCACTTTCCG 271
```

Fig. 1

α-CONOTOXIN PEPTIDES WITH ANALGESIC PROPERTIES

This invention relates to novel peptides of the alpha conotoxin (α-conotoxin) class and their use in the treatment or prevention of pain, in recovery from nerve injury and in the treatment of painful neurological conditions such as stroke. The invention also relates to pharmaceutical compositions comprising these peptides. The peptides of the invention are also useful as research reagents for investigation of nicotinic acetylcholine receptor physiology and pharmacology.

BACKGROUND OF THE INVENTION

All references, including any patents or patent applications, cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents forms part of the common general knowledge in the art, in Australia or in any other country.

Predatory marine snails of the genus *Conus* (cone snails) are a highly diverse family of marine molluscs which capture their prey by envenomation (Screenivasan, 2002). The venom of a typical cone snail is a complex mixture comprising about one hundred different peptides, which target different ion channels and receptors and interfere with their function, resulting in immobilisation of the prey (Olivera et al, 1990; Olivera and Cruz, 2001).

The mixture of peptides present depends on the species of cone snail and the prey on which it feeds, and may vary with time even in individual molluscs (Lewis et al 1994; Jones et al 1996; Bingham et al 1996). Classes of peptides found in *Conus* venoms include the α-, αA- and ψ-conotoxins (antagonists at nicotinic acetylcholine receptors), μ-, μO-conotoxins (antagonists at voltage-gated sodium ion channels), δ-conotoxins (agonists, which inhibit inactivation at voltage-sensitive sodium channels), ω-conotoxins (antagonists at voltage-sensitive calcium channels), κ- and κA-conotoxins (antagonists at potassium channels), σ-conotoxins (inhibitors of 5HT receptors), χ-conotoxins (inhibitors of noradrenaline uptake), conantokins and conodynes (antagonists at NMDA receptors), ρ-conotoxins (inhibitors of the α1-adrenoceptors), conorfamides (Maillo et al., 2001), and contulakins (inhibitors of neurotensin receptors). For review see Jones and Bulaj, 2000; McIntosh and Jones, 2001).

The α-conotoxins are typically found in cone snails which prey on fish or on marine snails or marine worms. They are typically 12-19 amino acids in length, and have four cysteine residues which form two disulfide bonds, forming a two-loop structure (McIntosh et al, 1999). They are characterised by an ability to inhibit the nicotinic acetylcholine receptor (nAChR). nAChRs are ligand-gated ion channels which consist of five subunits arranged around a cation-conducting pore (Sargent 1993; Lukas et al 1999; Karlin, 2002).

There are two main classes of nAChRs:

1) the neuronal type; and 2) the muscle type.

Neuronal type nAChRs are present both pre- and post-synaptically in the central and peripheral nervous systems, while the muscle type nAChRs are found post-synaptically at skeletal neuromuscular junctions (Wonnacott 1997). The main difference between these receptors is their subunit composition. The neuronal type receptors are formed from the combination of α and β subunits or α subunits alone, while the muscle type receptors are composed of α, β, γ and ε (or δ) subunits. The functional receptors have different combinations of subunits (see Karlin, 2002), and have a range of pharmacological properties (see Albuquerque et al., 1997; Lukas et al 1999 for review). Specific α-conotoxins display different affinity and selectivity for muscle and neuronal nAChRs and their subtypes.

Compounds of the α-conotoxin class may be useful in the treatment of disorders which involve the neuronal nAChR. The neuronal nAChR has been implicated in the pathophysiology of Alzheimer's disease (Guan et al, 2000), Parkinson's disease (Aubert et al, 1992), schizophrenia (Mukherjee et al, 1994), small cell lung carcinoma (Codignola et al, 1996) nicotine addiction (U.S. Pat. No. 5,780,433, U.S. Pat. No. 5,866,682), pain (Marubio et al 1999), and as neuromuscular blocking agents, such as muscle relaxants (U.S. Pat. No. 6,268,473 and U.S. Pat. No. 6,277,825) and in certain forms of epilepsy (Steinlein et al 1995).

Conotoxins of another class, the ω-conotoxin class, have provided lead compounds for stroke and for pain. ω-conotoxin MVIIA (Neurex SNX-111, Warner-Lambert CI-1009, or Elan's Ziconotide) and ω-conotoxin CVID (AMRAD AM336) are presently undergoing clinical trials for the treatment of manifestations of stroke (Zhao et al 1994; Heading, 1999; Shen et al 2000; Jones and Bulaj, 2000) and for chronic pain (Bowersox et al 1996; 1997; Jain, 2000; Jones and Bulaj, 2000). These compounds target N-type calcium channels in nerves. However, the members of the ω-conotoxin class still have undesirable side effects in some patients (Penn and Paice, 2000), and the US Food and Drug Administration has requested a repeat of the Stage III clinical trials for Ziconotide (re-named Prialt™ by Elan) for treatment of cancer pain.

Yet another class of conopeptide, the conantokins, having 10-30 amino acids, including preferably two or more γ-carboxyglutamic acid residues, have been developed for the treatment of neurological and psychiatric disorders, including pain, e.g., as an analgesic agent (U.S. Pat. No. 6,277,825). In addition, a novel class of conopeptide, whose target receptor is yet to be defined (McIntosh et al 2000), has been shown to have analgesic activity in the mouse.

We have recently found that a specific amino acid at position 10 ($Leu^{10}$) of α-conotoxin PnIB is responsible for conferring potency for the neuronal-type nicotinic response (Broxton et al 2000). We have also found that splice variants of the α-conotoxins PnIA and PnIB from *Conus pennaceus* show improved selectivity for α7 subunits of nAChRs (U.S. patent application Ser. No. 09/639,565; see also Hogg et al, 1999; Broxton et al, 2000).

We have now found that a previously unexamined *Conus* species, *Conus victoriae*, which is found along the north-western coast of Australia, has novel α-conotoxins with unexpectedly powerful analgesic activity. Surprisingly, the ability of one particular α-conotoxin (Vc1.1) to inhibit sensory nerve function, and consequently its analgesic activity, is even higher than that of ω-conotoxin MVIIA (ziconotide, Prialt™) from *Conus magus*. In addition, we have found that a post-translational modification of this peptide lacks analgesic activity but retains the ability of the parent compound to accelerate recovery from nerve injury. We have also identified two other new α-conotoxins, conotoxin An1.1 from *Conus anemone* and conotoxin Vg1.1 from *Conus virgo*, which have similar sequences to Vc1.1, and have similar pharmacological actions.

SUMMARY OF THE INVENTION

In a first aspect, the present invention provides an isolated α-conotoxin peptide comprising the following sequence of amino acids:

$Xaa_1$-Cys-Cys-Ser-$Xaa_2$-$Xaa_3$-$Xaa_4$-Cys-$Xaa_5$-$Xaa_6$-$Xaa_7$-$Xaa_8$-$Xaa_9$-$Xaa_{10}$-$Xaa_{11}$-Cys (SEQ ID NO:10) in which $Xaa_1$ is Gly or Asp $Xaa_3$ is Pro or hydroxyproline or Gln; each of $Xaa_2$, $Xaa_4$ to $Xaa_8$ and $Xaa_{11}$ is independently any amino acid; $Xaa_9$ is Pro, hydroxyproline or Gln; $Xaa_{10}$ is Asp, Glu or γ-carboxyglutamate; $Xaa_{11}$ is optionally absent; and the C-terminus is optionally amidated, with the proviso that the peptide is not α-conotoxin EpI or α-conotoxin ImI.

Preferably $Xaa_2$ is Asp, His or Asn; $Xaa_4$ is Ala, Pro or Arg; $Xaa_5$ is Asn, Ala or Tyr; $Xaa_6$ is Ala, Tyr, His, Met or Val; $Xaa_7$ is Asn or Asp; $Xaa_8$ is His or Asn; and $Xaa_{11}$ is Ile or Tyr.

More preferably the isolated α-conotoxin peptide comprises the following sequence of amino acids:

$Xaa_1$-Cys-Cys-Ser-$Xaa_2$-$Xaa_3$-$Xaa_4$-Cys-$Xaa_5$-$Xaa_6$-$Xaa_7$-$Xaa_8$-$Xaa_9$-$Xaa_{10}$-$Xaa_{11}$-Cys (SEQ ID NO:11)

in which $Xaa_1$ is Gly or Asp; $Xaa_2$ is Asp, His or Asn; $Xaa_3$ is Pro or 4-Hydroxyproline, $Xaa_4$ is Ala, Pro or Arg; $Xaa_5$ is Asn, Ala or Tyr; $Xaa_6$ is Ala, Tyr, His, Met or Val; $Xaa_7$ is Asn or Asp; $Xaa_8$ is His or Asn; $Xaa_9$ is Pro, hydroxyproline or Gln; $Xaa_{10}$ is Asp, Glu or γ-carboxyglutamate; $Xaa_{11}$ is Ile or Tyr; and the C-terminus is amidated. Even more preferably $Xaa_1$ is Gly or Asp, $Xaa_3$ is Arg, $Xaa_4$ is Asn, $Xaa_5$ is Tyr, $Xaa_6$ is Asp, $Xaa_7$ is His, and $Xaa_{10}$ is Ile.

Most preferably the peptide comprises the following sequence of amino acids:

Gly-Cys-Css-Ser-Asp-$Xaa_1$-Arg-Cys-Asn-Tyr-Asp-His-$Xaa_2$-$Xaa_3$-Ile-Cys [SEQ ID NO:1]

in which $Xaa_1$ is proline or hydroxyproline; $Xaa_2$ is proline, hydroxyproline or glutamine; $Xaa_3$ is aspartate, glutamate or γ-carboxyglutamate; and the C-terminus is optionally amidated. More preferably $Xaa_1$ is proline; $Xaa_2$ is proline and $Xaa_3$ is glutamate. The C terminus may be amidated, or may contain a free carboxylic acid group. Preferably the C terminus is amidated.

The peptide of the invention preferably has one or more of the following abilities:

(a) to inhibit a neuronal nicotinic acetylcholine receptor (nAChR), or (b) to act as an analgesic in mammals, or (c) to accelerate recovery from nerve injury. Preferably also the peptide does not affect muscle-type nicotinic responses in rats.

In particularly preferred embodiments, the peptide comprises the sequence set out in any one of

| | |
|---|---|
| GCCSDPRCNYDHPEIC-$NH_2$ | (SEQ ID NO:2) |
| GCCSD4-HypRCNYDHPgammacarboxy-GluIC-$NH_2$ | (SEQ ID NO:7) |
| DCCSNPPCAHNNPDC-$NH_2$; and | (SEQ ID NO:8) |
| GCCSHPACYANNQDYC-$NH_2$, | (SEQ ID NO:9) |

in each of which the C-terminal cysteine is amidated.

It will be clearly understood that the peptide may be isolated from a mollusc of the genus *Conus*, or may be synthetic or recombinant. One or more L-amino acids present in the naturally-occurring sequence may be replaced by its corresponding D-amino acid.

Preferably the peptide is synthetic, and may be prepared by methods known in the art, for example by conventional solid-phase peptide synthesis using BOC or fMOC methods. Where the peptide is isolated from a mollusc of the genus *Conus*, the *Conus* is preferably *Conus victoriae, Conus anemone* or *Conus virgo.*

It will also be clearly understood that all isomers of the peptide, including all disulfide connectivity forms (see Price-Carter et al 2002) are within the scope of the invention.

The four cysteine residues in the peptide are oxidized to provide two intramolecular disulfide bonds. Since this reaction proceeds spontaneously, the reduced form is a source of the active form. This linking of cysteine residues via disulfide bonds may occur in three alternative ways: first to second, first to third or first to fourth cysteine, followed by linking of the two remaining cysteines in each case (see Gehrmann et al 1998). Other possible sulphydryl linkings are those known to produce active peptide at the neuronal nicotinic receptor, such as the 4:6 link in α-conotoxin AuIB from *Conus aulicus* (Luo et al 1998), or the 4:3 loop found in α-conotoxin Im1 from *Conus imperialis* (McIntosh et al, 1994).

Preferably the peptide has four cysteine residues in a CC—$(X)_4$—C—$(X)_7$—(C) [SEQ ID NO:13], or so-called 4:7 loop framework in which the linking of the cysteine residues via disulfide bonds occurs with the first to third and second to fourth cysteine. Amino acid deletions give rise to smaller loops, which may also provide active peptides, for example, the 4:6 loop α-conotoxin AuIB from *Conus aulicus.*

The peptide bonds of the primary sequence would normally be of a trans geometry, but one or more peptide bonds may assume a cis geometry. Furthermore, the disulfide bonds themselves are chiral, and the particular geometry assumed by each disulfide bond allows up to four forms as a result of this source of isomerism (Lin et al., 1999). All of these forms are within the scope of the invention.

Some interconversion between the various isomers is feasible under physiological conditions, so that any isomer may be a source of the active form; the invention includes within its scope all fully reduced forms, all partially oxidized forms and all oxidized forms encompassed by the types of isomerism described above.

The invention also encompasses amino acid sequence variants of the specific sequences disclosed herein, including sequences which have undergone one or more amino acid substitutions, additions, deletions or side chain modifications, provided that the peptide retains the ability to inhibit the activity of a nAChR, which is preferably a neuronal nAChR, to prevent pain, and/or to accelerate recovery from nerve injury.

Such substitutions may have a different effect on activity. For example, we have found that γ-carboxylation of glutamate results in significant reduction in analgesic activity, but does not affect the ability of the peptide to accelerate recovery from nerve injury.

Other derivatives contemplated by the invention include glycosylation variants, ranging from a completely unglycosylated molecule to a modified glycosylated molecule. Altered glycosylation patterns may result from expression of recombinant molecules in different host cells. In one preferred embodiment, the C-terminal glycine of the precursor peptide (see FIG. 1) is removed and replaced by amidation of the C-terminal cysteine in the synthesized peptide, to imitate the C-terminus of known active α-conotoxins. Other specific post-translational modifications (PTMs) include hydroxylation of proline (eg. to give 4-hydroxy proline in Vc1.1ptm) and γ-carboxylation of the glutamate (see Bandyopadhyay et al., 2002), both of which we have engineered with Vc1.1ptm:

(SEQ ID NO:7)
GCCSD4 -HypRCNYDHPgammacarboxy-GluIC-$NH_2$ in which the C-terminus cysteine is amidated.

Still other PTMs which are known in conopeptides include 5-bromotryptophan for tryptophan, O-sulfated tyrosine for tyrosine, pyroglutamate for glutamate at the N-terminus (as in κA-conotoxin SIVA and μ-conotoxin PIIIA), threonine-O-gal(Nac)-Gal for threonine and D-tryptophan for tryptophan, and those described in International patent application No. WO00/44769.

In a preferred embodiment, the α-conotoxin peptide has the following sequence:

GCCSDPRCNYDHPEIC-$NH_2$ [SEQ ID NO: 2]

This preferred peptide is designated Vc1.1.

The peptides of the invention may be naturally-occurring conopeptides, or may be derivatives of such naturally-occurring peptides. The derivatives of the naturally-occurring conopeptides may differ from their naturally occurring counterparts by one or more amino acid substitutions, deletions or additions, as described below.

Substitutions encompass amino acid alterations in which an amino acid is replaced with a different naturally-occurring or a non-conventional amino acid residue. Such substitutions may be classified as "conservative", in which case an amino acid residue contained in a peptide is replaced with another naturally-occurring amino acid of similar character, for example Gly to Ala, Asp to Glu, Asn to Gln or Trp to Tyr. Possible alternative amino acids include serine or threonine, aspartate or glutamate or carboxyglutamate, proline or hydroxyproline, arginine or lysine, asparagine or histidine, histidine or asparagine, tyrosine or phenylalanine or tryptophan, aspartate or glutamate, isoleucine or leucine or valine.

It is to be understood that some non-conventional amino acids may also be suitable replacements for the naturally occurring amino acids. Substitutions encompassed by the present invention may also be "non-conservative", in which an amino acid residue which is present in a polypeptide is substituted with an amino acid having different properties, such as naturally-occurring amino acid from a different group (eg. substituting a charged or hydrophilic or hydrophobic amino acid with alanine), or alternatively, in which a naturally-occurring amino acid is substituted with a non-conventional amino acid. Additions encompass the addition of one or more naturally occurring or non-conventional amino acid residues. Deletions encompass the deletion of one or more amino acid residues.

Without wishing to limit the scope of the invention, it is presently believed that the cysteine residues and 3 to 4 consensus amino acids are likely to be essential to the biological activity of the molecule, and therefore the scope of substitution at these points may be limited, as discussed further below.

It is to be clearly understood that the invention also encompasses peptide analogues, which include but are not limited to the following:

1. Compounds in which one or more amino acids is replaced by its corresponding D-amino acid. The skilled person will be aware that retro-inverso amino acid sequences can be synthesised by standard methods; see for example Chorev and Goodman, 1993;

2. Peptidomimetic compounds, in which the peptide bond is replaced by a structure more resistant to metabolic degradation. See for example Olson et al, 1993; and 3. Compounds in which individual amino acids are replaced by analogous structures for example, gem-diaminoalkyl groups or alkylmalonyl groups, with or without modified termini or alkyl, acyl or amine substitutions to modify their charge.

The use of such alternative structures can provide significantly longer half-life in the body, since they are more resistant to breakdown under physiological conditions.

Methods for combinatorial synthesis of peptide analogues and for screening of peptides and peptide analogues are well known in the art (see for example Gallop et al, 1994; Hogan, 1997).

The peptides or peptidomimetics of the invention may be synthesised using standard solid phase techniques, such as Fmoc or BOC chemistry, followed by oxidative disulfide bond formation. Methods for the synthesis of conotoxins are known in the art; see for example Loughnan et al (1998), Groebe et al (1997), Favreau et al (1999), Miranda and Alewood, 1999. Following deprotection and cleavage from the solid support the reduced peptides may be purified using methods known in the art, such as preparative chromatography.

The peptide of the invention may also be prepared using recombinant DNA technology. A nucleotide sequence encoding the peptide sequence may be inserted into a suitable vector and protein expressed in an appropriate expression system. In some instances, further chemical modification of the expressed peptide may be appropriate, for example C-terminal amidation. Under some circumstances it may be desirable to undertake oxidative bond formation of the expressed peptide as a chemical step following peptide expression. This may be preceded by a reductive step to provide the unfolded peptide. Those skilled in the art will readily be able to determine appropriate conditions for the reduction and oxidation of the peptide.

Thus in a second aspect, the invention further provides an isolated or synthetic nucleic acid molecule comprising:

the nucleotide sequence set out in SEQ ID NO: 3 and FIG. 1:

(SEQ ID NO: 3)
ATGGGCATGCGGATGATGTTCACCGTGTTTCTGTTGGTTGTCTTGGCAAC
CACTGTCGTTTCCTCCACTTCAGGTCGTCGTGAATTTCGTGGCAGGAATG
CCGCAGCCAAAGCGTCTGACCTGGTCAGTTTGACCGACAAGAAGCGAGGA
TGCTGTAGTGATCCTCGCTGTAACTATGATCATCCAGAAATTTGTGGTTG
AAGACGCTGATGCTCCACGACCCTCTGAACCACGACACGCCGCCCTCTGC
CTGACCTGCTTCACTTTCCG;

(b) a nucleotide sequence complementary to that defined in (a); or (c) a nucleotide sequence able to hybridize to the sequence defined in either (a) or (b) under at least moderately stringent conditions.

(d) a nucleic acid molecule which has at least 75% sequence identity to (a).

More preferably in (c) the nucleic acid molecule is able to hybridise under stringent conditions to the molecule of (a). More preferably in (d) the nucleic acid molecule has at least about 75%, preferably at least 80%, even more preferably at least 90% sequence identity to the molecule of (a).

"Stringent conditions" for hybridization or annealing of nucleic acid molecules are those that (1) employ low ionic strength and high temperature for washing, for example 0.015 M NaCl/0.0015 M sodium citrate/0.1% sodium dodecyl sulfate (SDS) at 50□C, or (2) employ during hybridization a denaturing agent such as formamide, for example 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/mL), 0.1% SDS, and 10% dextran sulfate at 42° C., with washes at 42° C. in 0.2×SSC and 0.1% SDS.

Preferably the nucleic acid encodes peptide Vc1.1.

The nucleic acid molecules of the invention may be DNA or RNA. When the nucleic acid molecule is a DNA, it may be genomic DNA or cDNA. When the nucleic acid molecule is RNA, it is generally an mRNA. The nucleic acid molecules of the present invention may be integrated into or ligated to, or otherwise fused or associated with, other genetic molecules such as vectors, in particular expression vectors. Vectors and expression vectors are generally capable of replication and, if applicable, expression in one or both of a prokaryotic cell or a eukaryotic cell. Preferred prokaryotic cells include *E. coli, Bacillus* sp and *Pseudomonas* sp. Preferred eukaryotic cells include yeast, fungal, plant, mammalian and insect cells. Preferred bacterial expression systems (reviewed by Baneyx, 1999), which provide the special needs of the peptides referred to above, would include (1) strains of *Escherichia coli* coexpressing DnaK-DnaL or GroEL-GroES chaperones (Nichihara et al 1998; Castanie et al 1997; Thomas and Baneyx, 1996) to aid folding;

(2) strains that express disuphide isomerases and disulphide oxidoreductases to aid disulphide-bond formation (Qiu et al 1998); and (3) strains that express peptidyl prolyl cis/trans isomerases (Hottenrott et al 1997, Stoller et al 1995) to catalyse trans to cis isomerisation of prolyl residues.

In a third aspect the invention provides a probe for detection of nucleic acid encoding Vc1.1, comprising at least 15, preferably at least 20, more preferably at least 30 consecutive nucleotides from the sequence set out in SEQ ID NO:3. Preferably the probe has the sequence set out in SEQ ID NO: 5 or SEQ ID NO: 6.

In a fourth aspect, the invention provides a genetic construct comprising a vector portion and a nucleic acid encoding a peptide according to the invention. Preferably the nucleic acid is operably linked to a promoter on the vector, so that the promoter is capable of directing expression of the nucleic acid in an appropriate cell.

In a fifth aspect, the invention provides a composition comprising a peptide according to the invention, together with a physiologically acceptable carrier. In one preferred embodiment, the carrier is a pharmaceutically acceptable carrier, and the composition is suitable for administration to a mammalian subject. In a second preferred embodiment, the carrier is suitable for use in tissue cultures or in experimental tests of nicotinic acetylcholine receptor function.

It is contemplated that the peptide of the invention is suitable both for pharmaceutical use and as a research reagent in assessment of nicotinic acetylcholine receptor function and other physiological parameters. In particular, the peptide is useful in modulating a particular subset of sensory neurones (small unmyelinated C fibres) which represents the first order neurone in the pain-conducting pathway for investigating the role of these receptors.

In a sixth aspect, the invention provides a method of treatment of a condition mediated by a nAChR, comprising the step of administering an effective amount of a peptide of the invention to a mammal in need of such treatment.

Preferably the condition is mediated by a neuronal nAChR. More preferably the condition is selected from the group consisting of stroke, pain, epilepsy, nicotine addiction, schizophrenia, Parkinson's disease, small cell lung carcinoma and Alzheimer's disease. An extended list of such conditions is given in U.S. Pat. No. 6,265,541.

Most preferably the condition is pain, which may result from any condition associated with neurogenic or neuropathic pain, including but not limited to cancer pain, post-surgical pain, oral or dental pain, referred trigeminal neuralgia, post-herpetic neuralgia, phantom limb pain, fibromyalgia, reflex sympathetic dystrophy and neurogenic pain conditions, including pain associated with inflammatory conditions such as rheumatoid arthritis and other inflammatory arthritides; or degenerative arthritis, e.g. osteoarthritis.

In a preferred embodiment, the invention further provides a method of treating or preventing pain, comprising the step of administering an effective amount of a peptide of the invention to a mammal in need of such treatment.

In a seventh aspect the invention provides a method of accelerating functional recovery from nerve injury, comprising the step of administering an effective amount of a peptide of the invention to a mammal in need of such treatment.

The term "functional recovery" is to be understood to mean a return of function to normal. We have found that Vc1.1 and Vc1.1 ptm enhance (or "accelerate") the rate at which this process occurs, ie functional recovery returns sooner than would otherwise have been the case; a faster return than with saline control or with MVIIA is observed.

The mammal may be a human, or may be a domestic or companion animal. While it is particularly contemplated that the compounds of the invention are suitable for use in medical treatment of humans, they are also applicable to veterinary treatment, including treatment of companion animals such as dogs and cats, and domestic animals such as horses, cattle and sheep, or zoo animals such as felids, canids, bovids, and ungulates.

The compounds and compositions of the invention may be administered by any suitable route, and the person skilled in the art will readily be able to determine the most suitable route and dose for the condition to be treated. Dosage will be at the discretion of the attendant physician or veterinarian, and will depend on the nature and state of the condition to be treated, the age and general state of health of the subject to be treated, the route of administration, and any previous treatment which may have been administered.

The carrier or diluent, and other excipients, will depend on the route of administration, and again the person skilled in the art will readily be able to determine the most suitable formulation for each particular case.

Methods and pharmaceutical carriers for preparation of pharmaceutical compositions are well known in the art, as set out in textbooks such as Remington's Pharmaceutical Sciences, 17th Edition, Mack Publishing Company, Easton, Pa., USA.

The peptide may be delivered using any suitable delivery means, including oral administration; injection, either subcutaneously, intravenously, intra-arterially, intrathecally, intracerebrally, intramuscularly; or via microencapsulation (see for example U.S. Pat. Nos. 4,352,883; 4,353,888; 5,084,350); macroencapsulation (see for example U.S. Pat. Nos. 5,284,761; 5,158,881, 4,976,859); topical lotions or delivery via a vector or an osmotic pump, or via iontophoretic or electrophoretic means.

We have demonstrated that peptide Vc1.1 inhibits the neuronal nAChR, and has analgesic activity. It is not yet known whether the activity of the peptide of the invention is mediated by actual binding of the peptide to the target receptor, or whether it otherwise interferes with receptor activity. However, we have shown that the in vitro actions of the peptide are consistent with a competitive mode of action with nicotinic agonists, and are not mediated via voltage-activated ion channels. Further, the peptide does not inhibit the muscle-type nicotinic acetylcholine responses. For example, Vc1.1 did not inbibit the release of noradrenaline or adrenaline from bovine chromaffin cells in culture when stimulated by 56 mM $K^+$ (see FIG. 3). Our results, obtained using a rat model to investigate the effect of the compound on sensory nerve activity, indicate that Vc1.1 is more effective than MVIIA in inhibiting sensory nerve activity as demonstrated by a decrease in the inflammatory vascular response, which is dependent on sensory peptide release from sensory nerves (see FIGS. 9*a* and *b*). Additional results, obtained using a rat model of neuropathic pain, indicate that the peptide of the invention has superior and longer lasting activity than MVIIA and previously-known conopeptides, and is suitable for parenteral administration (see FIGS. 6 and 7). Moreover, so far we have not observed any adverse side-effects, and the rats utilised in the experiments were alive 10 months after completion of the treatment. The peptide did not have any effect on resting systemic blood pressure in the rat (see FIG. 15).

For the purposes of this specification it will be clearly understood that the word "comprising" means "including but not limited to", and that the word "comprises" has a corresponding meaning.

BRIEF DESCRIPTION OF THE FIGURES

FIG. 1 shows the DNA and amino acid sequence of the conopeptide precursor for peptide Vc1.1. The active toxin region is underlined, and the primer sequence is indicated in bold. The toxin region is 16 amino acids in length, and includes four cysteine residues in a CC—$X_{(4)}$—C—$X_{(7)}$—C arrangement. The asterisk indicates the stop codon; the glycine at the C-terminus is typically lost in forming the C-terminus amidated Vc1.1 peptide.

FIG. 2*a* shows the results of an experiment using Vc1.1 at 0.01 μM, 0.1 μM, 1 μM, and 10 μM and stimulation with nicotine at 4 μM.

(a) Vascular responses to electrical stimulation of sensory nerves. The bars represent mean±SEM (n=6–8). The asterisks denote significant difference compared to the control group ($p<0.05$).

(b) Effect of α-conotoxin Vc1.1 on the vascular effects of sodium nitroprusside (SNP), a direct-acting smooth muscle vasodilator.

Figure 8A:
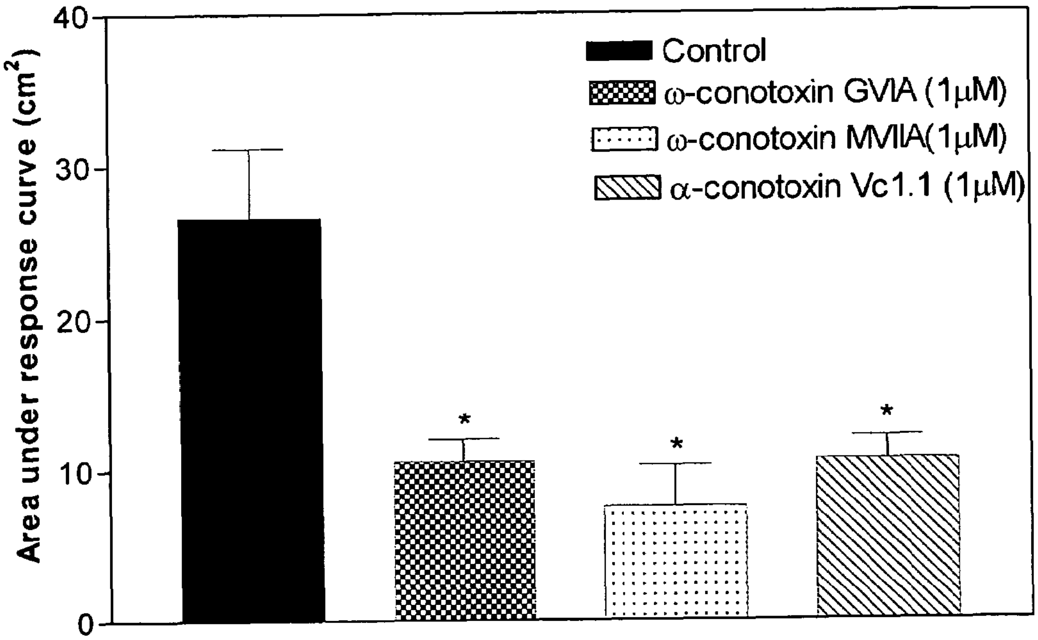
FIG. 8 illustrates the effect of conotoxins on microvascular blood flow in rat skin.
Figure 9A:
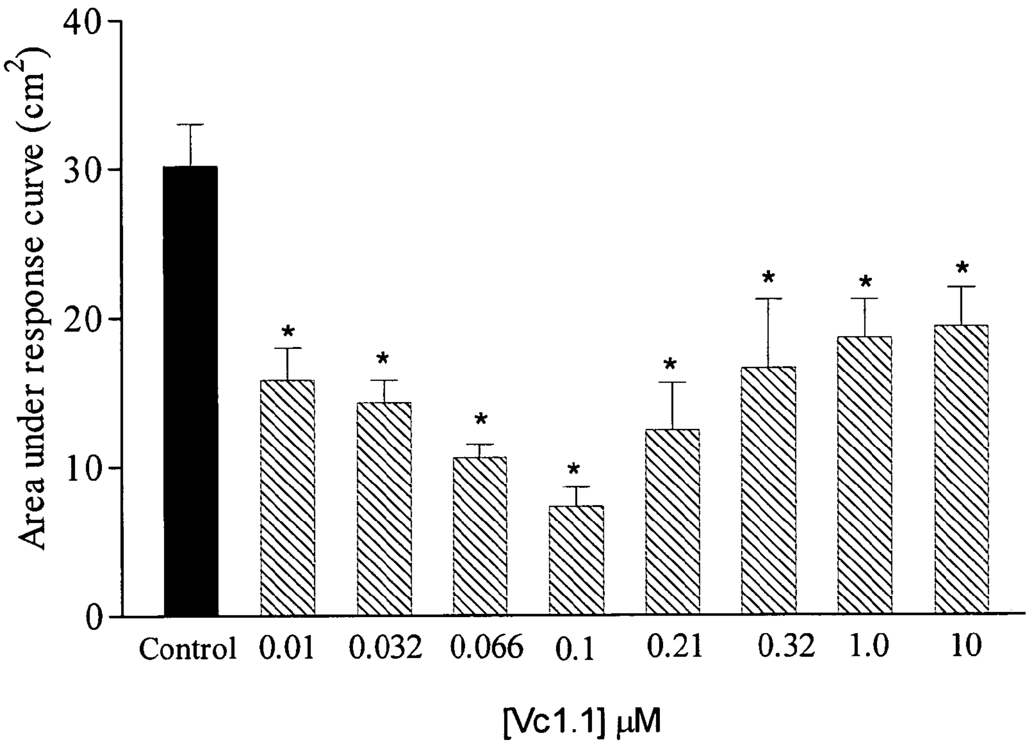

FIG. 9*a* illustrates the dose-response effect of Vc1.1 on sensory nerve activity. The experiments were conducted as in FIG. 8*a*, but in addition to 1 μM Vc1.1 a range of concentrations of Vc1.1 was compared. The results show that Vc1.1 is effective in inhibiting the vascular response to sensory nerve activation with 0.1 μM concentration being the most effective.

Figure 9B:
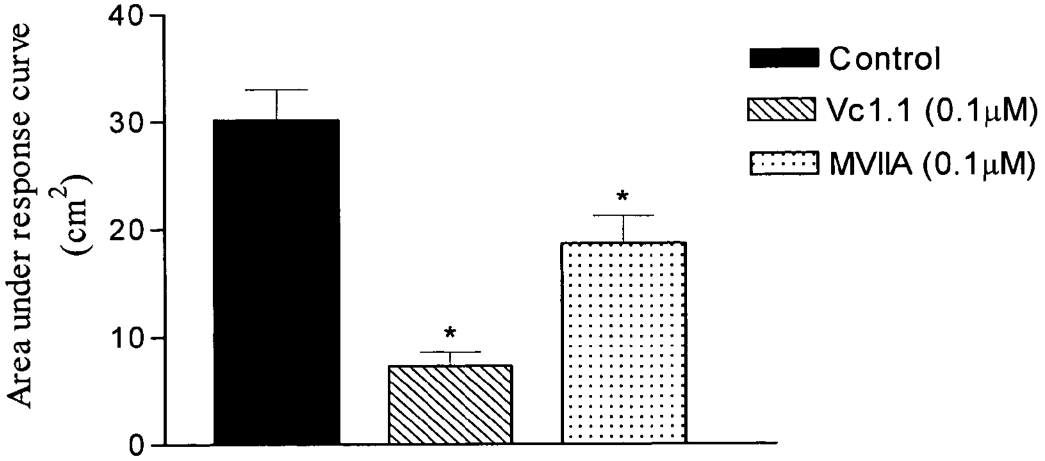

FIG. 9*b* compares the effectiveness of Vc1.1 and MVIIA in inhibition of sensory nerve activity (both at a concentration of 0.1 μM peptide). Vc1.1 is more potent than MVIIA at this lower concentration, whereas at 1 μM peptide (FIG. 8*a*) MVIIA was more effective)

Figure 10A:
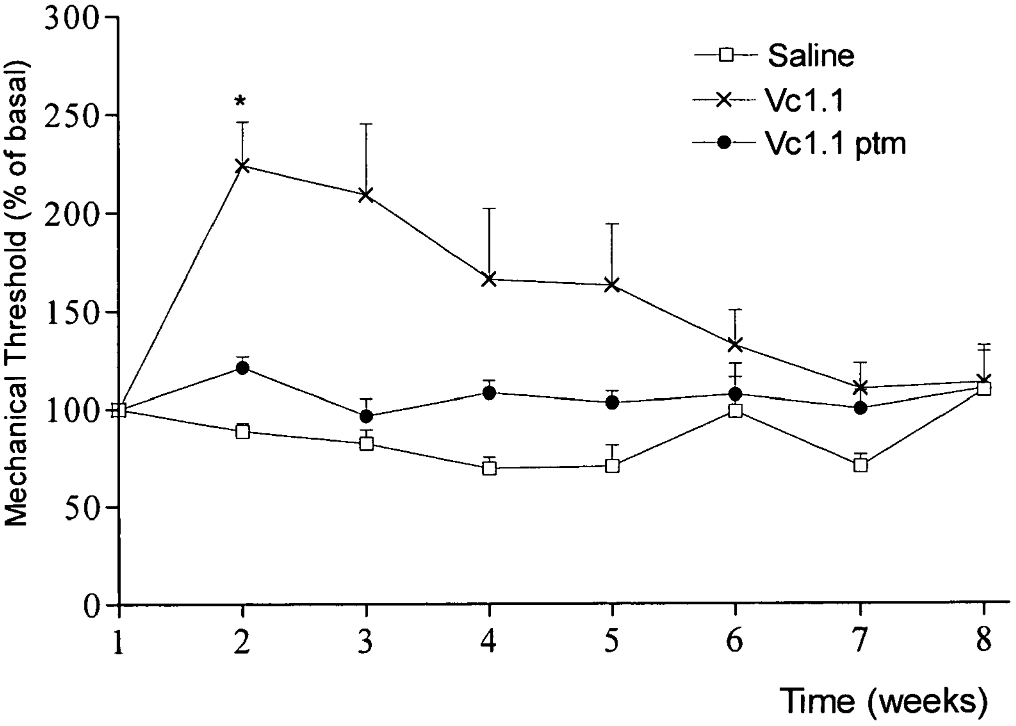

FIG. 10*a* compares the long-term effectiveness of Vc1.1 and Vc1.1ptm in inhibiting neuropathic pain when administered intramuscularly at 0.36 μg/200 μl and 0.37 μg/200 μl for Vc1.1 and Vc1.1ptm, respectively. The bars represent mean+SEM (n=6–8). The asterisks denote significant difference compared to the saline control group ($p<0.05$) The results indicate that Vc1.1 but not Vc1.1ptm was effective in inhibiting neuropathic pain for up to 5 weeks after injection.

Figure 10B:
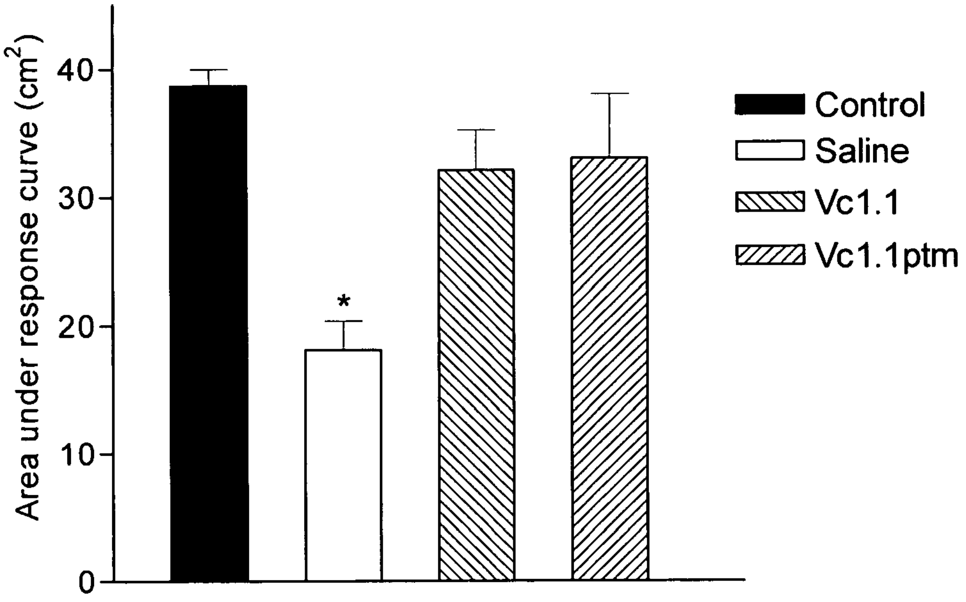

FIG. 10*b* compares the effectiveness of Vc1.1 and Vc1.1ptm given intramuscularly (im) in accelerating functional recovery of injured nerves, as assessed by their ability to mount an inflammatory vascular response.

Figure 11A:
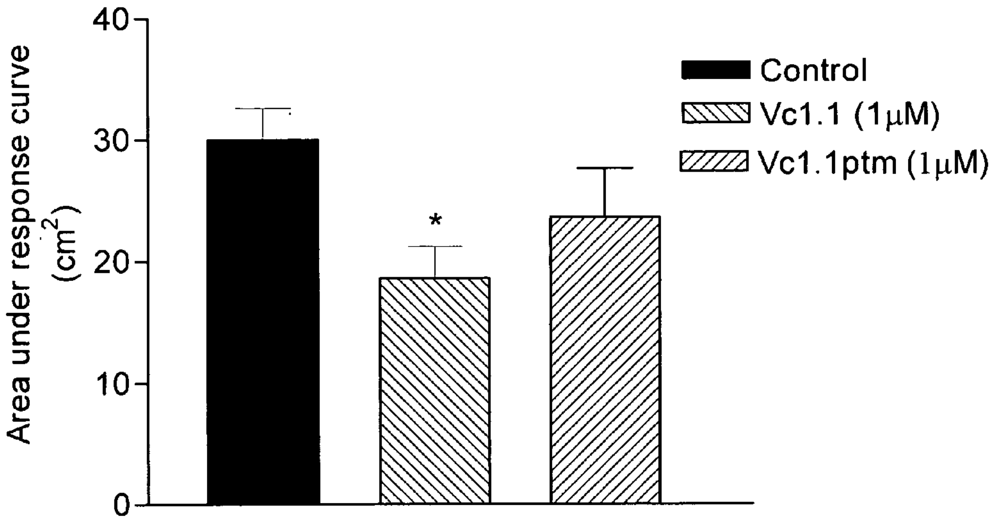

FIG. 11 compares the effectiveness of Vc1.1ptm and Vc1.1 in inhibiting sensory nerve activity. FIG. 11*a* shows that Vc1.1ptm is less effective than Vc1.1 at inhibiting sensory nerve activity when tested immediately after 30 minutes of superfusion with the peptide or saline.

Figure 11B:
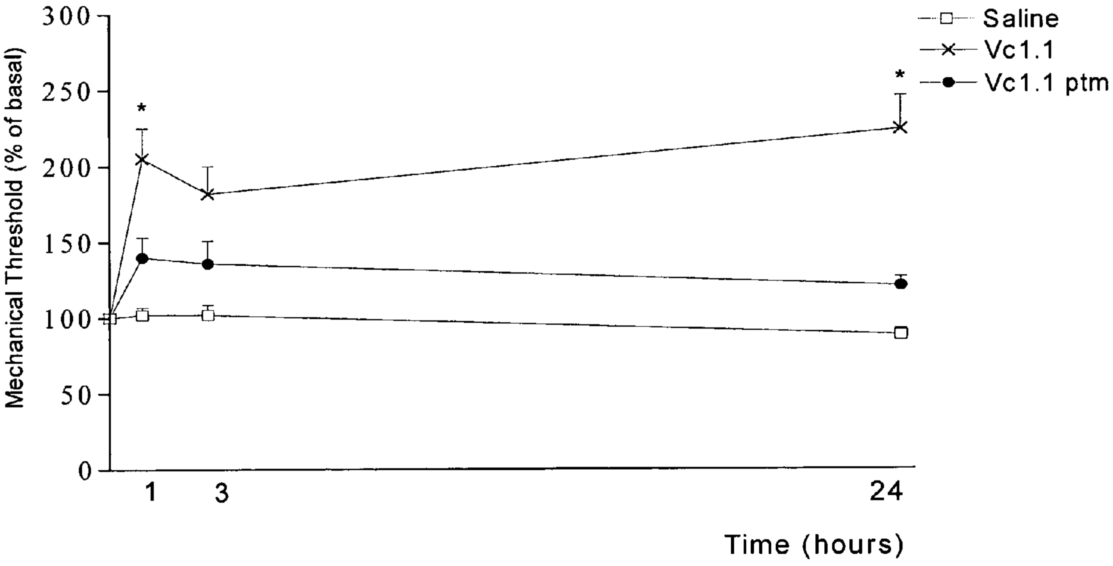

FIG. 11*b* shows that Vc1.1ptm is less effective than Vc1.1 at inhibiting sensory nerve activity up to 24 hours after the 30 minutes superfusion with the peptide or saline. The concentration was 0.36 μg/200 μl for Vc1.1 and 0.37 μg/200 μl for Vc1.1ptm.

FIG. 12 illustrates the effectiveness of Vc1.1, An1.1, Vg1.1, MVIIA, and Vc1.1ptm in inhibiting neuropathic pain (CCI model) over the following periods: a) Short-term (0-24 h), (b) 7-14 days, and (c) Long-term (2-8 weeks). FIG. 12(*d*) compares the effectiveness of Vc1.1, An1.1, MVIIA, and Vc1.1ptm to bring about functional recovery of the injured nerve, as assessed by their ability to mount an inflammatory vascular response.

Figure 13A:
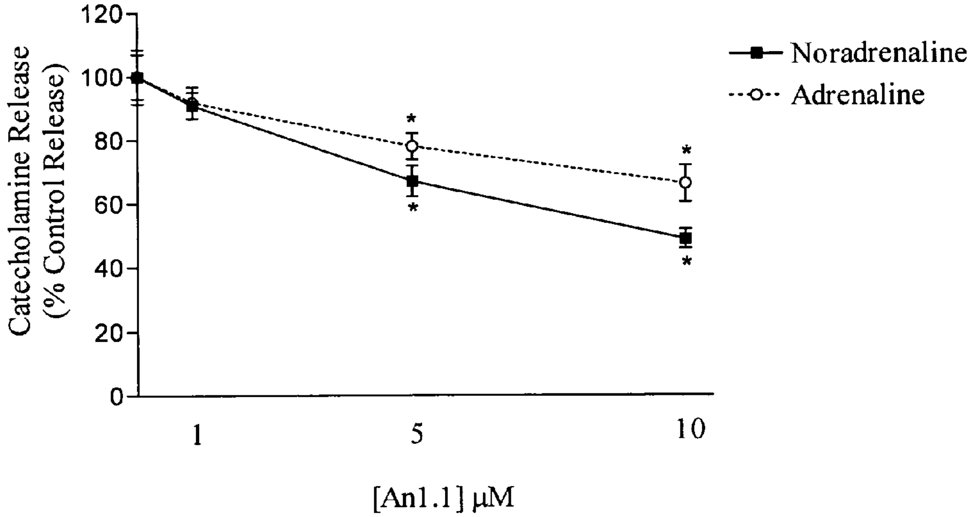
Figure 14A:
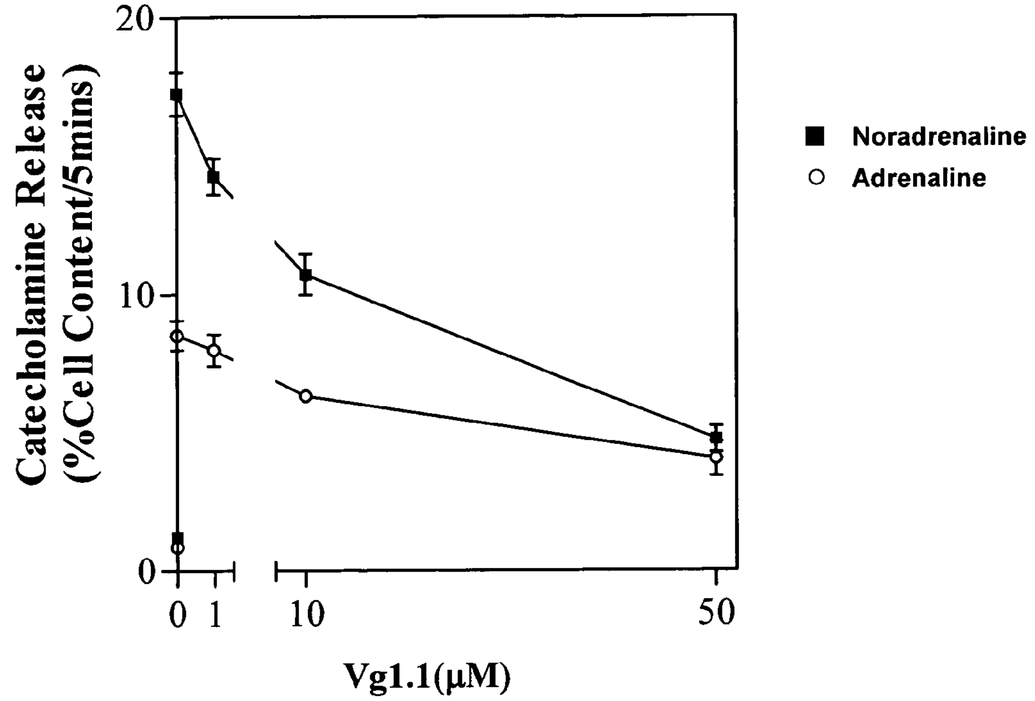

FIG. 13*a* illustrates the inhibition of the neuronal nicotinic response in cultured BCCs by An1.1, which was not nearly as inhibitory as Vc1.1 (compare with FIG. 2), or with Vg1.1 (see FIG. 14*a*).

Figure 13B:
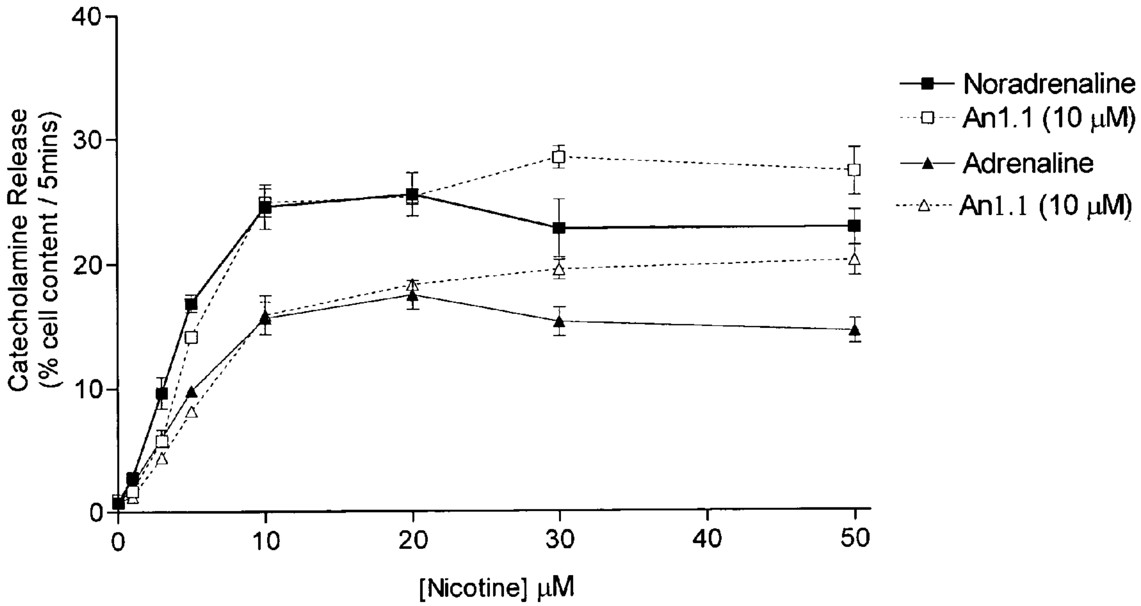

FIG. 13*b* shows that An1.1 is also a competitive inhibitor of the functional nicotinic receptor response in BCCs, and protects against nicotinic receptor desensitisation caused by high concentrations of nicotine.

Figure 14B:
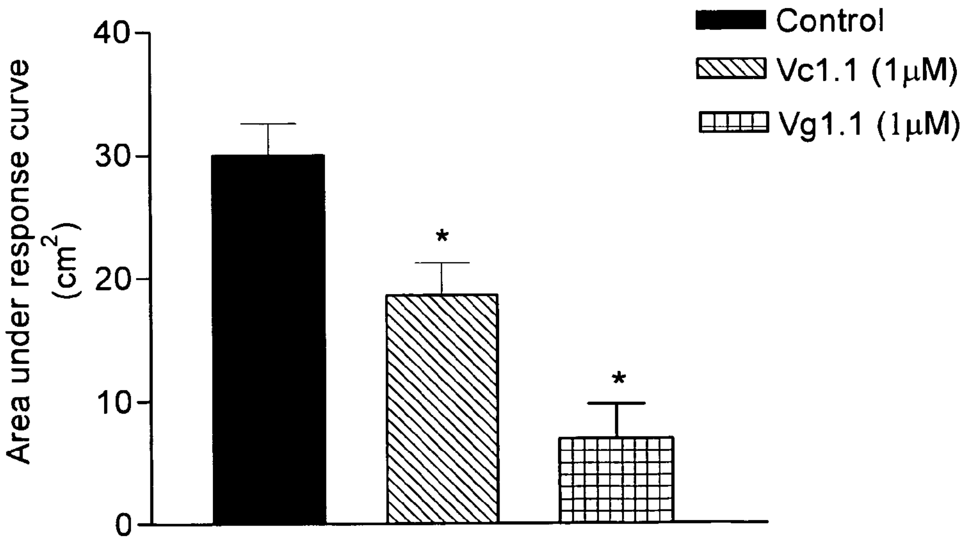
Figure 14C:
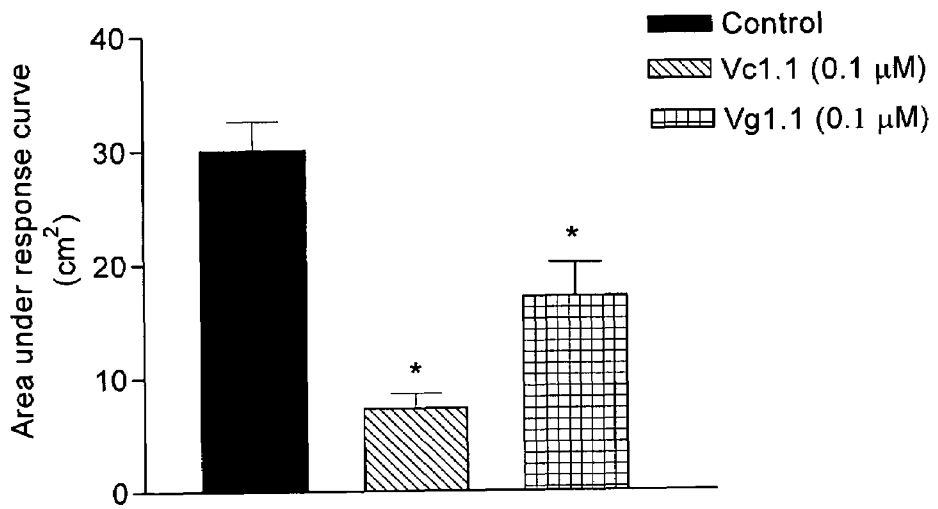

FIG. 14(*a*) illustrates the effect of the peptide α-conotoxin Vg1.1 on nicotine (1 μM)-evoked release of catecholamines (noradrenaline and adrenaline) from BCCs.

FIG. 14(*b*) is a comparison of the effects of Vg1.1 and Vc1.1 (both at 1.0 μM) on stimulation-induced vascular response in the rat (also compare with FIG. 8*a*). FIG. 14(*c*) is the same as (*b*), but at the lower dose of 0.1 μM, where Vc1.1 is now more effective than Vg1.1 (also compare with FIG. 9*b*).

Figure 15:
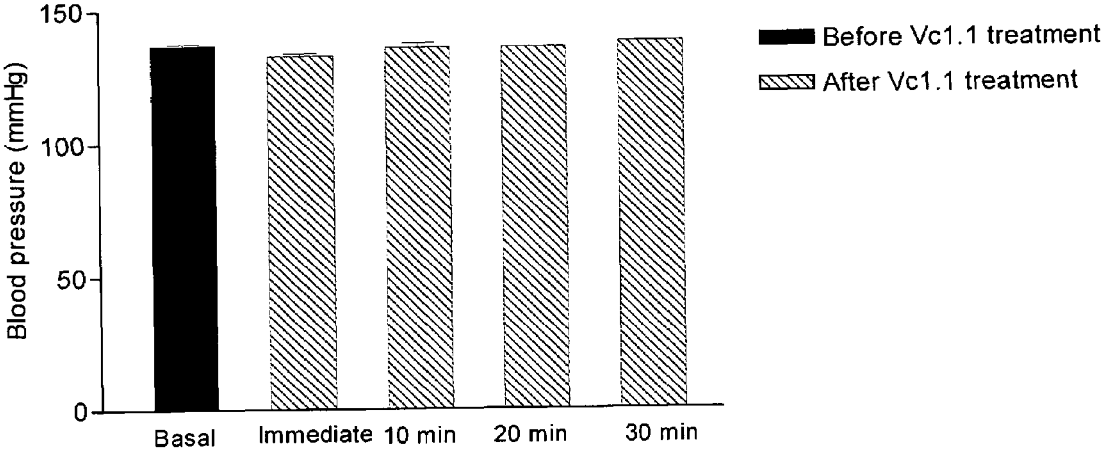

FIG. 15 shows that Vc1.1 (1 μM in 200 μl im) has no effect upon systemic blood pressure, ie. Vc1.1 does not have a systemic circulatory effect.

DETAILED DESCRIPTION OF THE INVENTION

For the purposes of this specification, the term "peptide and peptide analogue" includes compounds made up of units which have an amino and carboxy terminus separated in a 1,2, 1,3, 1,4 or larger substitution pattern. This includes the 20 naturally-occurring or "common" α-amino acids, in either the L or D configuration, the biosynthetically-available or "uncommon" amino acids not usually found in proteins, such as 4-hydroxyproline, 5-hydroxylysine, citrulline and ornithine; synthetically-derived α-amino acids, such as α-methylalanine, norleucine, norvaline, $C_\alpha$- and N-alkylated amino acids, homocysteine, and homoserine; and many others as known in the art.

This term also includes compounds that have an amine and carboxyl functional group separated in a 1,3 or larger substitution pattern, such as β-alanine, γ-amino butyric acid, Freidinger lactam (Freidinger et al, 1982), the bicyclic dipeptide (BTD) (Freidinger et al, 1982; Nagai and Sato, 1985), amino-methyl benzoic acid (Smythe and von Itzstein, 1994), and others well known in the art. Statine-like isosteres, hydroxyethylene isosteres, reduced amide bond isosteres, thioamide isosteres, urea isosteres, carbamate isosteres, thioether isosteres, vinyl isosteres and other amide bond isosteres known to the art are also useful for the purposes of the invention.

A "common" amino acid is an L-amino acid selected from the group consisting of glycine, leucine, isoleucine, valine, alanine, phenylalanine, tyrosine, tryptophan, aspartate, asparagine, glutamate, glutamine, cysteine, methionine, arginine, lysine, proline, serine, threonine and histidine. These are referred to herein by their conventional three-letter or one-letter abbreviations.

An "uncommon" amino acid includes, but is not restricted to, one selected from the group consisting of D-amino acids, homo-amino acids, N-alkyl amino acids, dehydroamino acids, aromatic amino acids (other than phenylalanine, tyrosine and tryptophan), ortho-, meta- or para-aminobenzoic acid, ornithine, citrulline, norleucine, γ-glutamic acid, aminobutyric acid (Abu), and α, α-disubstituted amino acids.

As stated above, the present invention includes peptides in which one or more of the amino acids has undergone side-chain modifications. Examples of side-chain modifications contemplated by the invention include modifications of amino groups such as reductive alkylation by reaction with an aldehyde followed by reduction with $NaBH_4$; amidination with methylacetimidate; acylation with acetic anhydride; carbamoylation of amino groups with cyanate; modification of amino groups with 2,4,6-trinitrobenzene sulphonic acid (TNBS); and acylation of amino groups with succinic anhydride and tetrahydrophthalic anhydride. The carboxyl group may be modified by carbodiimide activation via O-acylisourea formation followed by subsequent derivatisation, for example to a corresponding amide. Sulphydryl groups may be modified by methods such as carboxymethylation with iodoacetic acid or iodoacetamide; performic acid oxidation to cysteic acid; formation of a mixed disulfide with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. Any modification of a cysteine residue must not affect the ability of the peptide to form the necessary disulfide bonds. However, it is possible to replace the sulphydryl group of cysteine with the selenium equivalent, a selenohydryl group, so that the peptide forms a diselenium bond in place of one or more of the disulfide bonds.

Tryptophan residues may be modified, for example, by oxidation with N-bromosuccinimide or alkylation of the indole ring with 2-hydroxy-5-nitrobenzyl bromide or sulfenyl halides. Tyrosine residues may be in a sulfated or phosphorylated form. A non-exhaustive list of amino acids having modified side chains and other modified or non-naturally occurring amino acids is set out in Table 1.

TABLE 1

| Non-conventional amino acid | Abbrev. |
|---|---|
| α-aminobutyric acid | Abu |
| α-amino-α-methylbutyrate | Mgabu |
| aminocyclopropanecarboxylate | Cpro |
| aminoisobutyric acid | Aib |
| aminonorbornylcarboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |

TABLE 1-continued

| Non-conventional amino acid | Abbrev. |
|---|---|
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | arg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl)carbamylmethyl)glycine | Nnbhm |
| 1-carboxy-1-(2,2-diphenyl ethylamino)cyclopropane | Nmbc |
| N-cyclobutylglycine | Ncbut |
| N-cycloheptylglycine | Nchep |
| N-cyclohexylglycine | Nchex |

TABLE 1-continued

| Non-conventional amino acid | Abbrev. |
|---|---|
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylomithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl)carbamylmethyl)glycine | Nnbhe |
| L-O-methyl serine | Omser |
| L-O-methyl homoserine | Omhser |

These types of modifications may be useful to stabilise the peptide following administration to a subject. Other modifications may be made to the peptide in order to stabilise it or to enhance its other properties, for example membrane penetration or solubility. Such modifications include modifying the side chain of one or more amino acids to attach other types of group, for example one or more lipophilic groups. Such attachment may be made through a linking group designed to space the other group or groups away from the peptide so as not to interfere with the activity of the peptide. All such modified forms of the peptide are within the scope of the invention, provided that the modified peptide retains the ability to inhibit the activity of a nAChR, to prevent pain, and/or accelerate the rate of recovery from nerve injury. Those skilled in the art will readily be able to determine how to modify the peptides of the invention, and to identify those modified peptides which have the necessary activity.

For oral administration the active ingredients may require protection before administration. For example, the peptide may be formulated with an assimilable edible carrier, or the peptide may be enclosed in hard or soft shell gelatin capsule, or compressed into tablets, or incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations preferably contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin maybe added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. In addition, the active compound(s) may be incorporated into sustained-release preparations and formulations.

The pharmaceutical forms suitable for injectable use include sterile injectable solutions or dispersions, and sterile powders for the extemporaneous preparation of sterile injectable solutions. The solvent or dispersion medium for the injectable solution or dispersion may contain any of the conventional solvent or carrier systems for peptide actives, and may contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmolality, for example, sugars or sodium chloride. Prolonged absorption of the injectable compositions can be achieved by the use in the compositions of agents delaying absorption, for example, aluminum monostearate and gelatin. Pharmaceutical forms suitable for injectable use may be delivered by any appropriate route including intravenous, intramuscular, intraperitoneal, subcutaneous, intracerebral, intrathecal, epidural injection or infusion.

The present invention also extends to any other forms suitable for administration, for example topical application such as creams, lotions and gels, or compositions suitable for inhalation or intranasal delivery, for example solutions or dry powders.

Parenteral dosage forms are preferred, including those suitable for intravenous, intrathecal, intracerebral, intramuscular, intraperitoneal, subcutaneous or epidural delivery. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. A unit dosage form can, for example, contain the principal active compound in amounts ranging from 0.25 μg to about 2000 mg. Expressed in proportions, the active compound is generally present from about 0.25 μg/ml to about 200 mg/ml of carrier. In the case of compositions containing supplementary active ingredients, the dosages are determined by reference to the usual dose and manner of administration of the said ingredients.

Peptide Vc1.1 was identified through the application of the following molecular biology techniques to *Conus victoriae*. A cDNA library was created from mRNA isolated from venom duct tissue. Oligonucleotide primers were used to amplify α-conotoxin precursors using the polymerase chain reaction. The PCR product was cloned into a suitable plasmid vector and individual clones sequenced. The amino acid sequence encoded by the cDNA was then elucidated. This is described in further detail in Example 1.

Peptide Vc1.1 inhibits the neuronal nAChR. This was determined using a bovine chromaffin cell neuronal nAChR assay system. Bovine chromaffin cells are known to express neuronal nAChRs (Campos-Caro et al, 1997). When stimulated with nicotine the catecholamines noradrenaline and adrenaline are released. Chromaffin cells were isolated from the bovine adrenal medulla (Livett et al 1987a) and stimulated with nicotine in the presence of the peptide Vc1.1. Catecholamines released by chromaffin cells were separated using reverse phase high performance liquid chromatography and quantitated using electrochemical detection (Livett et al 1987b). It was found that the peptide Vc1.1 inhibited catecholamine release evoked by nicotine. This is described in Example 2.

Peptide Vc1.1 also has analgesic activity. The chronic constriction injury model (CCI) of Bennett and Xie (1987) was used to test the ability of Vc1.1 to inhibit mechanically induced hyperalgesia in rats. Rats were anesthetized and the right sciatic nerve exposed and tied with four chromic gut ligatures. This procedure produces hyperalgesia in the rat's paw. Rats were then injected intramuscularly in the mid thigh region with either saline or saline containing Vc1.1 A Basile Analgesy-Meter (Ugo Basile, Comerio, Italy), which exerts a force that increases at a constant rate, was used to apply pressure to the rat's paw. The force applied before the rat withdrew its paw was measured. It was found that following intramuscular administration of Vc1.1, nerve induced mechanical hyperalgesia was significantly attenuated both in the short (1-24 hrs) and long term (day 1-21). The ability of Vc1.1 to reduce mechanically induced hyperalgesia was compared with ω-MVIIA, a conotoxin that has been reported to be 1000 times more potent than morphine (Bowersox et al, 1996). Vc1.1 was found to be approximately 3 times more effective than ω-MVIIA at relieving mechanically induced hyperalgesia. This is described in Example 3.

Peptide Vc1.1 is also effective in inhibiting sensory nerve function as determined by measuring the vascular response to nerve stimulation. Microvascular blood flow was measured in the skin using laser Doppler flowmetry from the base of blisters raised on the hind footpad of anaesthetized rats using a suction pressure of −40 kPa. Sensory nerve modulation of vascular function was assessed using antidromic electrical nerve stimulation performed on a sciatic nerve preparation and by perfusing sensory neuropeptides over the blister base. This is described in Example 4.

Peptide Vc 1.1 and its post-translationally modified form (SEQ ID NO. 7) were also effective in accelerating the rate of recovery from nerve injury. This is discussed in Example 5.

The invention will now be described in detail by way of reference only to the following non-limiting examples and drawings.

EXAMPLE 1

Isolation of Peptide Vc1.1

(a) mRNA Extraction and cDNA Synthesis

Specimens of the cone snail *Conus victoriae* were collected from Broome, Western Australia. The snails were part of the legal by-catch of a commercial fisherman, and approximately 20 snails were used. The venom ducts and bulbs of the cone snails were removed by dissection, before being snap-frozen in liquid nitrogen. Poly-A mRNA was extracted using a Dynabeads mRNA Direct Kit in accordance with the manufacturer's specifications. Double-stranded cDNA was prepared from the isolated mRNA utilising a Marathon™ cDNA amplification kit. First strand DNA was constructed utilising the Marathon cDNA synthesis primer and Moloney murine leukaemia virus reverse transcriptase. Second strand DNA synthesis was achieved using *E. coli* DNA polymerase, *E. coli* DNA ligase and *E. coli* RNase H. Blunt ended double stranded cDNA was prepared using T4 DNA polymerase.

(b) PCR Amplification of DNA Encoding Vc1.1

DNA encoding the Vc1.1 was amplified using oligonucleotide primers designed to anneal to the 5' pre region

5'-ATGGGCATGCGGATGATGTT-3' (SEQ ID NO: 5)

and the 3' untranslated region

5'-CGGAAAGTGAAGCAGGTCAG-3'. (SEQ ID NO: 6)

The PCR contained 5 U of Taq polymerase (Hoffmann-La Roche); 5 μl of 10× reaction buffer (100 mM Tris-HCl, 15 mM $MgCl_2$, 500 mM KCl, pH 8.3); 400 μg of primers; 2 μl of 10 mM dNTPs; and an appropriate amount of cDNA in a total volume of 50 μl of milliQ water. The conditions for the PCR reaction were: 94° C. for 2 min; followed by 30 cycles of 94° C. for 30 sec, an annealing step of 55° C. for 30 sec, 72° C. for 45 sec; concluding with a final step of 72° C. for 5 mins.

(c) Cloning of Vc1.1 DNA 50 ng PCR product was ligated into the pCR2.1 vector (Original TA Cloning® Kit) at a molar ratio of 2:1. The reaction mixture was incubated overnight at 14° C. in a final volume of 10 μl of 6 mM Tris-HCl, pH7.5, 6 mM $MgCl_2$, 5 mM NaCl, 0.1 $mg.ml^{-1}$ BSA, 7 mM β-mercaptoethanol, 0.1 mM ATP, 2 mM dithiothreitol, 1 mM spermidine with 4 U of T4 DNA ligase. The pCR2.1 plasmid was transformed into competent INVαF'*E. coli* cells in accordance with the manufacturer's specifications (Original TA Cloning® Kit). Cells were then spread onto LB plates containing ampicillin and X-gal (5-bromo-4-chloro-3-indolyl-β-D-galactoside). Recombinant colonies were selected, incubated overnight at 37° C. in LB broth, and screened using a UltraClean™ Mini Plasmid Prep Kit in accordance with the manufacturer's protocols.

(d) Sequencing of DNA Fragments Encoding Vc1.1

Clones containing inserts of interest were identified by agarose gel electrophoresis and sequenced by the dideoxy chain termination method using an ABI PRISM Dye Terminator Cycle Sequence Ready Reaction Kit. A GeneAmp PCR System 2400 (Perkin Elmer) was used for thermal cycling. Each sequencing reaction underwent 25 cycles of: 96° C. for 10 sec, 50° C. for 5 sec, 60° C. for 4 min. Sequences were analysed on a Perkin Elmer 377 sequencer.

The nucleotide sequence of the clone encoding Vc1.1 (SEQ ID NO: 3) and deduced amino acid sequence for the Vc1.1 precursor protein (up to the stop codon) (SEQ ID NO: 4) are shown in FIG. 1. The nucleotide sequence giving rise to the deduced mature peptide is underlined, and the stop codon TGA immediately follows the underlined sequence. This sequence has the following characteristics:

(a) The coding sequence is the first 201 base pairs up to and including a stop codon of SEQ ID NO:3.

(b) The coding sequence translates to 66 amino acid residues:

```
                                    (SEQ ID NO: 4)
M G M R M M F T V F L L V V L A T T V V
S S T S G R R E F R G R N A A A K A S D
L V S L T D K K R G C C S D P R C N Y D
H P E I C G;
```

the mature toxin region is underlined.

(c) the synthesised 16 amino acid residue peptide Vc1.1 (SEQ ID NO: 2) derives from the 17 amino acid residues preceding the STOP codon, with the C-terminal glycine residue usually being removed and replaced by amidation of the resulting C-terminal cysteine, consistent with the C-terminus of known α-conotoxins which are active as neuronal nAChR antagonists.

(d) The synthesized peptide has four cysteine residues in a CC—$(X)_4$—C—$(X)_7$—C framework.

EXAMPLE 2

Peptide Vc1.1 Inhibits Nicotine-evoked Catecholamine Release

Adrenal chromaffin cells were isolated from adult bovine adrenal glands as described by Livett et al., (1987a). Isolated cells were plated out on collagen coated 24-well plates at a density of $2.8\times10^5$ cells/$cm^2$.

Three- to four-day old cultured chromaffin cells were allowed to equilibrate to room temperature for 5 mins. The incubation media was removed by two consecutive washes in Locke's buffer (154 mM NaCl, 2.6 mM KCl, 2.15 mM $K_2HPO_4$, 0.85 mM KH2PO$_4$, 10 mM D-glucose, 1.18 mM $MgSO_4.7H_2O$, 2.2 mM $CaCl_2.2H_2O$, 0.5% bovine serum albumin, pH 7.4) for five mins. Cells were then incubated with various concentrations (0.01 μM, 0.1 μM, 1 μM, 10 μM) of the peptide Vc1.1 for five mins, before stimulation with either 4 μM nicotine or 56 mM KCl for a further five mins. The incubation mixture was separated from the cells and acidified with 2M perchloric acid (PCA) to give a final concentration of 0.4M PCA. The catecholamines remaining in the chromaffin cells were released by lysing the cells with 0.01M PCA, and then acidified by addition of an equal volume of 0.8M PCA. Precipitated proteins were removed by centrifugation at 10,000 rpm for 10 mins. To measure the basal release of catecholamines, a control containing neither nicotine, KCl or Vc1.1 was used. To determine the maximal release of catecholamines, a second control was stimulated with 4 μM nicotine or 56 mM KCl in the absence of Vc1.1.

Figure 2A:
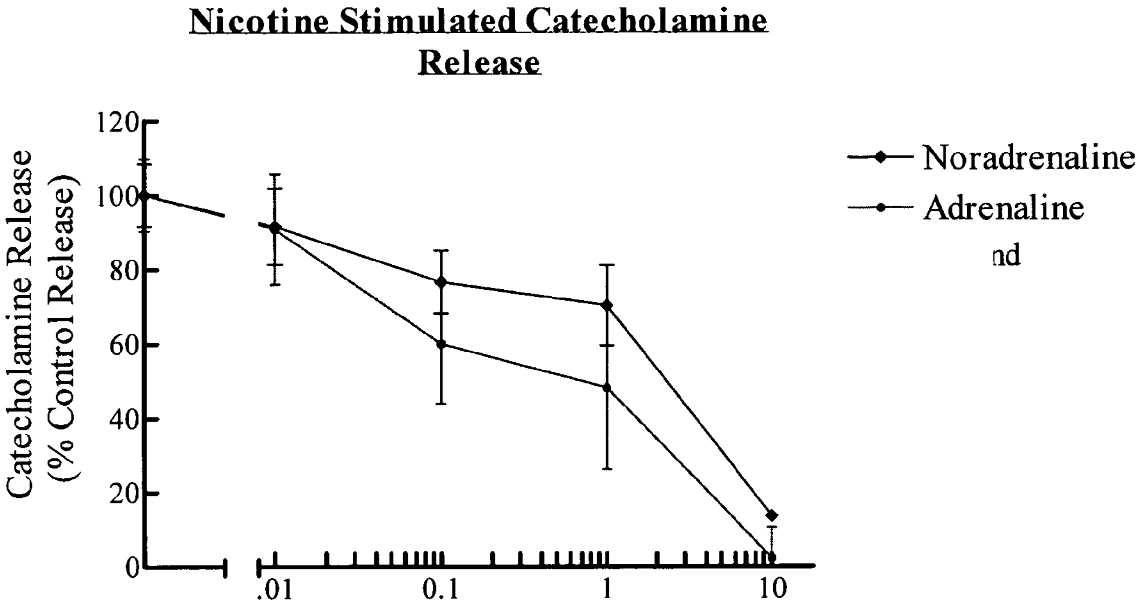
FIGS. 2*a* and *b* show concentration-response curves for the action of Vc 1.1 on nicotine-stimulated catecholamine release from bovine chromaffin cells. Chromaffin cell cultures, 4-5 days old, were preincubated with Vc1.1 at 0.01 μM, 0.1 μM, 1 μM, 5 μM and 10 μM for five minutes before stimulation with nicotine.
Figure 2B:
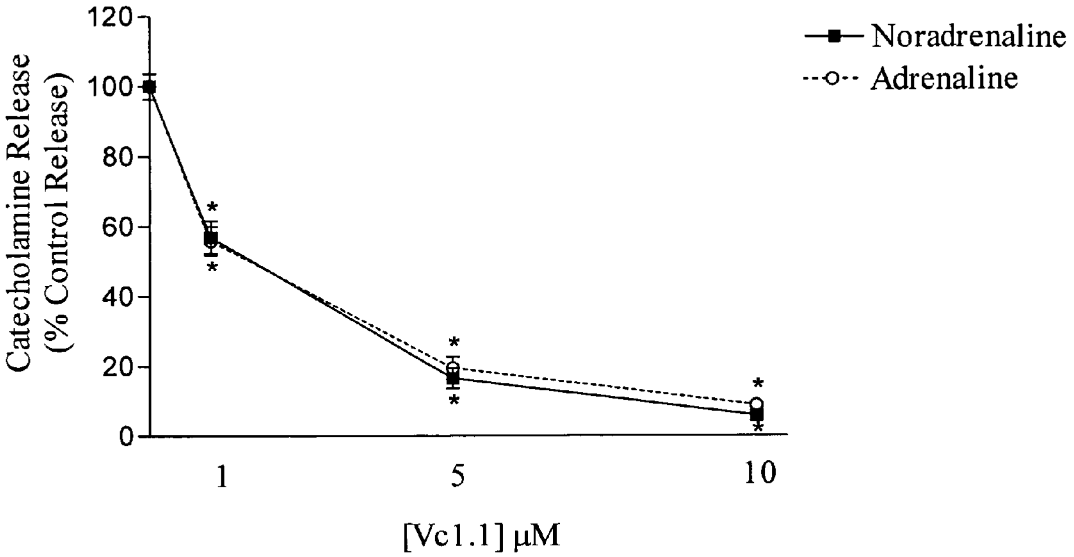
FIG. 2*b* shows the results of a second experiment using Vc1.1 at 1 μm, 5 μM and 10 μM, and stimulation with nicotine at 1 μM.
Figure 2C:
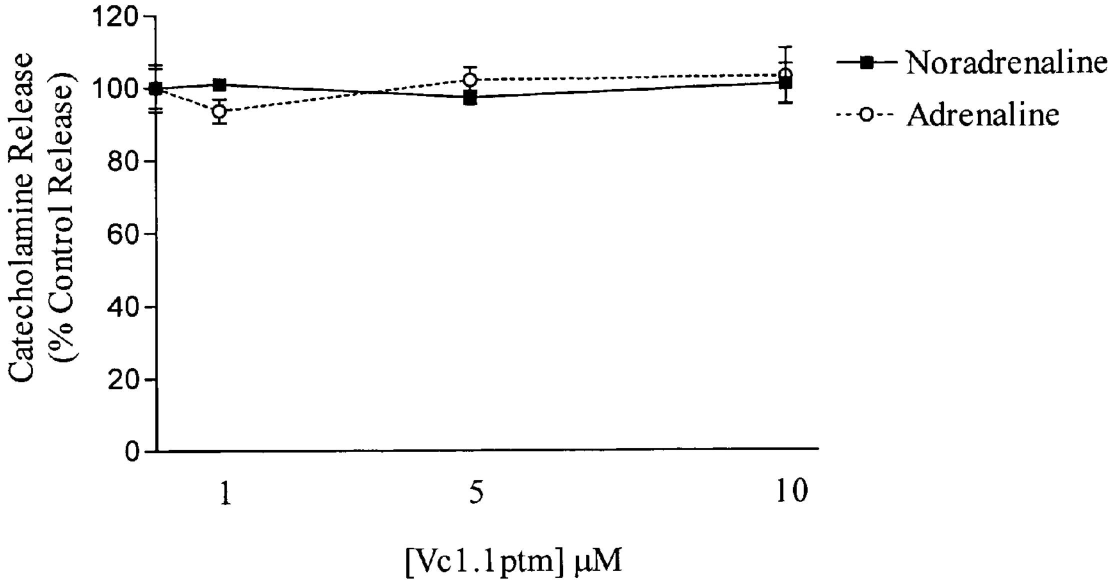
FIG. 2*c* shows the results of an experiment performed as for FIG. 2*b*, but where Vc1.1ptm was used in place of Vc1.1. Results are expressed as mean±standard deviation (n=4). The $IC_{50}$ for adrenaline and noradrenaline release is approximately 1-3 μM.

Catecholamines present in each sample were separated by reverse phase high performance liquid chromatography (RP-HPLC) utilizing a C18 column (Bio-Rad; 150 mm×4.6 mm, 5 μm particle size) and isocratic elution with 10% methanol in the mobile phase (70 mM $KH_2PO_4$, 0.1 mM NaEDTA, 0.2% heptane sulphonic acid). Catecholamines eluting from the column were identified by their retention time, and quantified by electrochemical detection (650 mV BAS model LC-3A). Known adrenaline and noradrenaline standards were used to calculate the amount of catecholamines in each sample, and these were expressed as a percentage of the total cell content. The results are shown in FIG. 2.

Consistent with its membership in an A-lineage superfamily, this novel α-conotoxin was a potent inhibitor of the nicotinic response in an in vitro cell-based functional assay for the neuronal-type nicotinic receptor, but did not inhibit the response due to 56 mM $K^+$, indicating that voltage-activated ion channels such as the N-type voltage-gated $Ca^{++}$ ion channels which are the target for the ω-conotoxins such as ziconotide are unlikely to be involved.

Figure 3:
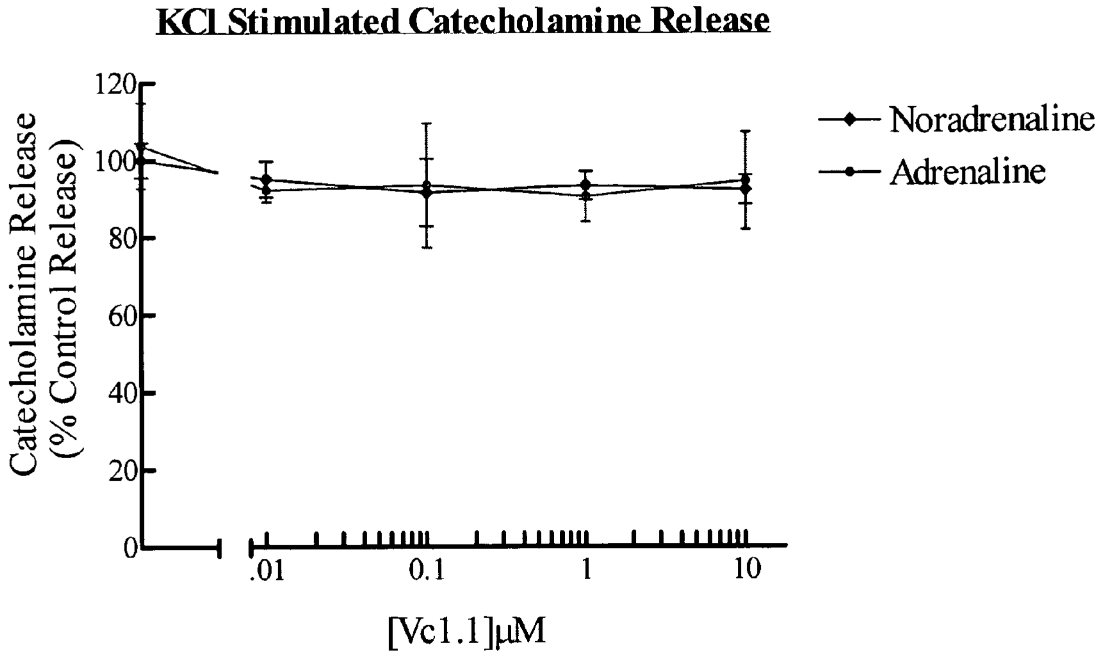
FIG. 3 shows the concentration-response curve for the action of Vc 1.1 on KCl-stimulated catecholamine release from chromaffin cells. Chromaffin cell cultures, 4-5 days old, were preincubated with Vc1.1 at 0.01 μM, 0.1 μM, 1 μM, and 10 μM for five minutes before stimulation with KCl (56 mM).
Figure 4:
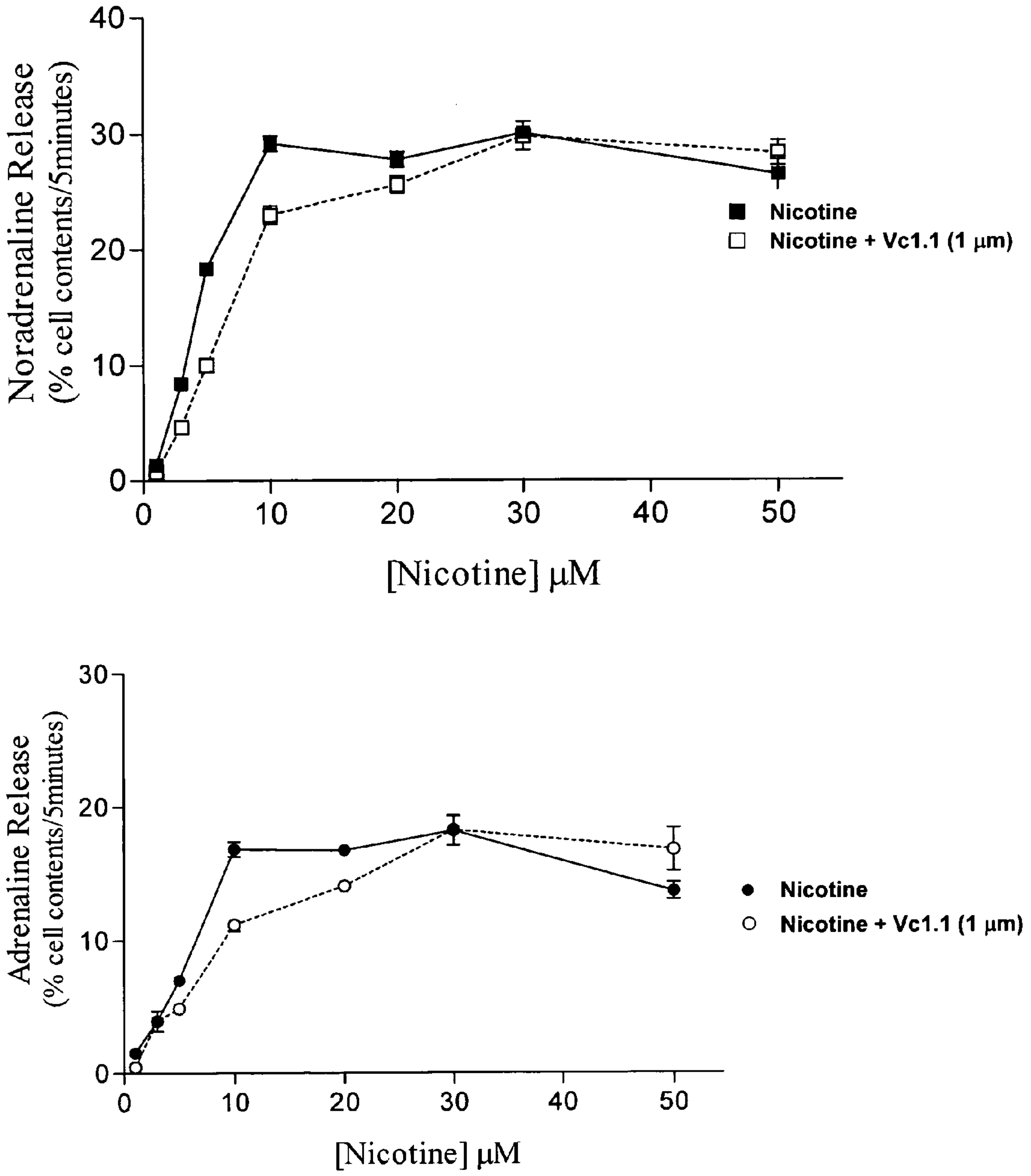
FIG. 4 illustrates the competitive nature of the inhibition of nicotine-evoked release of catecholamines (noradrenaline and adrenaline) from bovine adrenal chromaffin cells by Vc1.1 (1 μM). The results indicate that Vc1.1 competes with nicotine for action at the functional nicotinic receptor. Nicotine at high concentrations (>20 μM) is able to overcome the inhibition by Vc1.1.

Thus it was found that Vc1.1 inhibited catecholamine release evoked by nicotine. At a concentration of 10 μM Vc1.1 inhibited noradrenaline release by 86% and adrenaline release by 97%. The $IC_{50}$ of Vc1.1 was calculated to be 1-3 μM. Vc1.1 did not have an inhibitory action when catecholamine release was evoked with KCl, as shown in FIG. 3. This demonstrated that Vc1.1 does not target voltage gated ion channels, and confirmed that it targets the nicotinic acetylcholine receptor.

EXAMPLE 3

Vc1.1 Displaces $^3$H-epibatidine (a Nicotinic Receptor Agonist) from its Binding Site on the nAChR Bovine adrenal glands obtained from the local abattoir were dissected and the medulla removed and placed into ice-cold 10% w/v 0.32M sucrose buffer, supplemented with 1 mM EDTA, 0.1 mM PMSF and 0.01% sodium azide. The medulla was homogenised using a Polytron homogeniser, and the homogenate centrifuged at 100 g for 10 minutes at 4° C. The resultant supernatant was decanted (S1) and the pellet resuspended in ice-cold sucrose buffer (5 ml/g of original medulla weight). This resuspended pellet was centrifuged at 100 g for 10 minutes at 4° C. and the supernatants S1 and S2 were combined and centrifuged at 12000 g for 30 minutes at 4° C. The resultant pellet was resuspended in 50 μM phosphate buffer (40 mM $K_2HPO_4$, 10 mM $KH_2PO_4$) containing 0.01% sodium azide, 0.1 mM PMSF and 1 mM bovine serum albumin and centrifuged at 12000 g for 30 minutes at 4° C. This step was repeated and the washed pellet resuspended in 50 mM phosphate buffer and stored at −70° C. A Bradford assay was performed to determine protein concentration, using bovine serum albumin as standard.

This study used 3H-epibatidine (3H-epi) and other ligands in binding studies for pharmacological characterisation of the nAChRs expressed on bovine adrenal medullary membranes. Epibatidine has a high affinity for neuronal nAChRs, particularly those containing α3, but a low affinity for α7 nAChRs (Gerzanich et al 1995). The stored adrenal medulla membranes were thawed and incubated (300-500 μg protein/tube) at 37° C., for 2 hours in the presence of 1 nM $^3$H-epibatidine and the test ligand (concentration range 1 nM-1 mM). $^3$H-epibatidine was the radioligand, of choice as it has broad nAChR subtype affinity. After the incubation period each assay tube was filtered and washed with phosphate buffered saline (150 mM NaCl, 8 mM $K_2HPO_4$, 2 mM $KH2PO_4$) in a Brandell filtration system. Glass fibre filters used in the filtration step had previously been soaked overnight in phosphate-buffered saline containing 5% polyethylene imine (PEI). The bound radioactivity remaining on the membranes was quantitated by liquid scintillation. Non-specific binding was that remaining on the membranes after displacement with 2 mM nicotine. Total binding was obtained by substituting the displacing test ligand with milliQ water. Specific binding was determined by subtracting the non-specific from the total binding. Saturation binding experiments (n=3) determined a Kd value using non-linear regression analysis (Prism, GraphPad, San Diego, Calif.). From the displacement experiments Hill coefficients and Ki values were determined using non-linear regression analysis. Ki values were determined using the Cheng-Prusoff rule whereby: $Ki=IC50/(1+[^3H\text{-epibatidine}])/Kd$ of $^3$H-epibatidine.

Our results show that $^3$H-epibatidine binding to bovine adrenal medullary membranes fits a single affinity model with a Hill coefficient of 1.08. Vc1.1 and Vc1.1ptm were examined for their ability to displace $^3$H-epibatidine. The plasma membranes are known to contain neuronal α-nAChRs.

Figure 5:
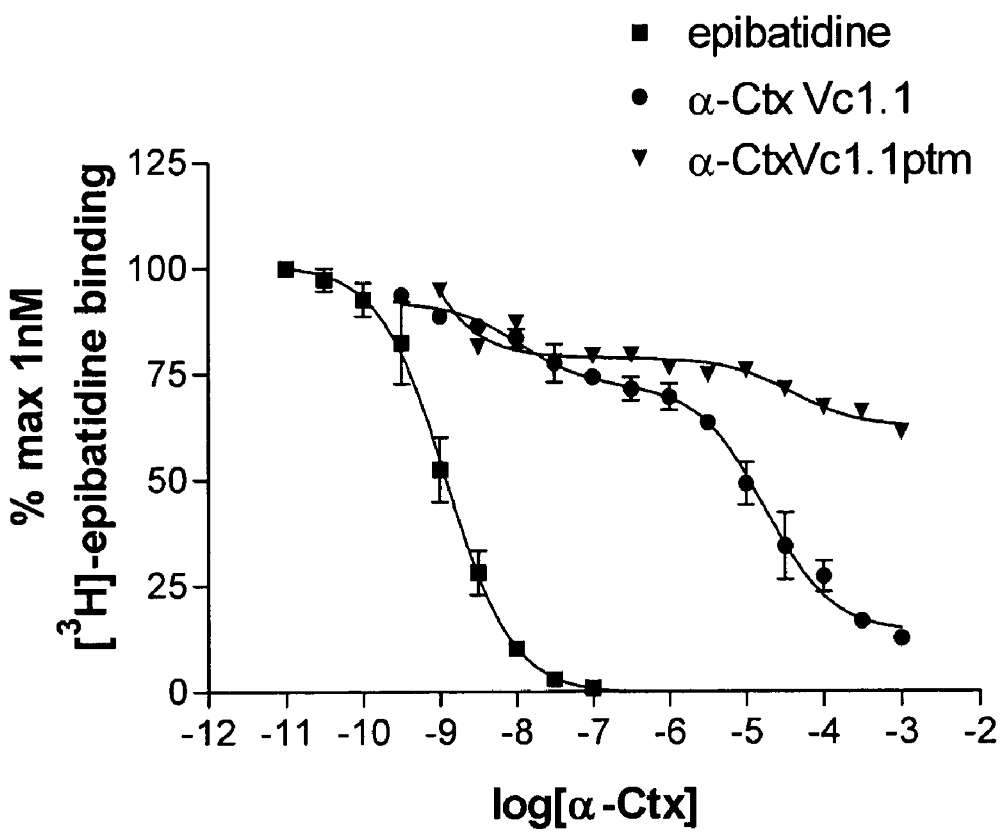
FIG. 5 shows that Vc1.1 competes for the binding of the labeled nicotinic receptor agonist, 3H-epibatidine. The biphasic nature of the competition binding curves indicates two distinct receptor components, a high affinity component and a lower affinity component, and the competitive nature of the inhibition of nicotine-evoked release of catecholamines from bovine adrenal chromaffin cells by Vc1.1 (1 μM). The results indicate that Vc1.1 competes with nicotine for action at the functional nicotinic receptor.

As shown in FIG. 5, α-conotoxin Vc01 displaced $^3$H-epibatidine binding, whereas Vc1.1ptm did not. Conotoxin Vc1.1 displaced the binding of the non-selective nicotinic receptor ligand $^3$H-epibatidine in a concentration-dependent manner, displaying both a high affinity and a lower affinity two-component binding profile. Vc1.1ptm displaced the first component, but did not significantly displace the second component of the binding, suggesting that two distinct binding sites may be involved in the binding of Vc1.1 to these membranes. This differential action of Vc1.1 and Vc1.1ptm is also apparent in FIG. 7, where Vc1.1 inhibits a painful stimulus but Vc1.1ptm is without effect.

In other studies we have found that cytosine, 1,1-dimethyl-4-phenylpiperazinium iodide (DMPP), carbachol, and nicotine, but not the α7 selective ligands, α-conotoxin ImI (purchased commercially from SIGMA or AUSpep) and α-bungarotoxin, displaced 3H-epibatidine binding. Taken together, these studies indicate that Vc01 probably binds to receptors of the α3α4 or α3α5α4 subtypes, whereas the receptor population not labelled by $^3$H-epi most probably contains the α7 subtype, perhaps in combination with other subunits.

EXAMPLE 4

Vc1.1 has Analgesic Activity (a) Chronic Constriction Injury Model

A unilateral peripheral neuropathy was produced by the Chronic Constriction Injury (CCI) method of Bennett and Xie (1987). Rats (n=4-8 per group) were anaesthetized with sodium pentobarbital (60 mg/kg). The right sciatic nerve was exposed at the level of the middle of the thigh by blunt dissection through the biceps femoris muscle. Proximal to the sciatic trifurcation, about 7 mm of nerve was freed of adhering tissue and 4 ligatures (4.0 chromic gut) were tied loosely around it with about 1 mm spacing. The skin incision was closed using surgical clips. Groups of control rats received sham procedures, in which the right sciatic nerves were isolated but not ligated.

(b) Measurement of Mechanical Pain Threshold

A synthetic form of ω-conotoxin MVIIA (SNX-111; Bowersox et al., 1996) was purchased from Auspep Pty Ltd, Animals were allowed to recover for one week before being injected intramuscularly at the mid thigh region with saline, or with either Vc1.1 or the synthetic ω-conotoxin MVIIA dissolved in 0.2 ml saline. Mechanical pain thresholds were determined with a slightly modified version of the Randall-Selitto method (Randall and Selitto, 1957), using the Basile Analgesy-Meter (Ugo Basile, Comerio, Italy). This instrument exerts a force on the rat's paw, which increases at a constant rate (a certain number of grams per second). The animal was restrained gently between cupped hands, and calibrated pressure increased until the rat withdrew its hind paw. Mechanical pain thresholds were measured before drug injection, 1,3 and 24 hours post-injection, and then daily over 7 days. After 7 days of drug treatment, intramuscular injections ceased, and the pain threshold was measured twice a week.

(c) Effect of Vc1.1 on Mechanically-induced Hyperalgesia

Figure 6A:
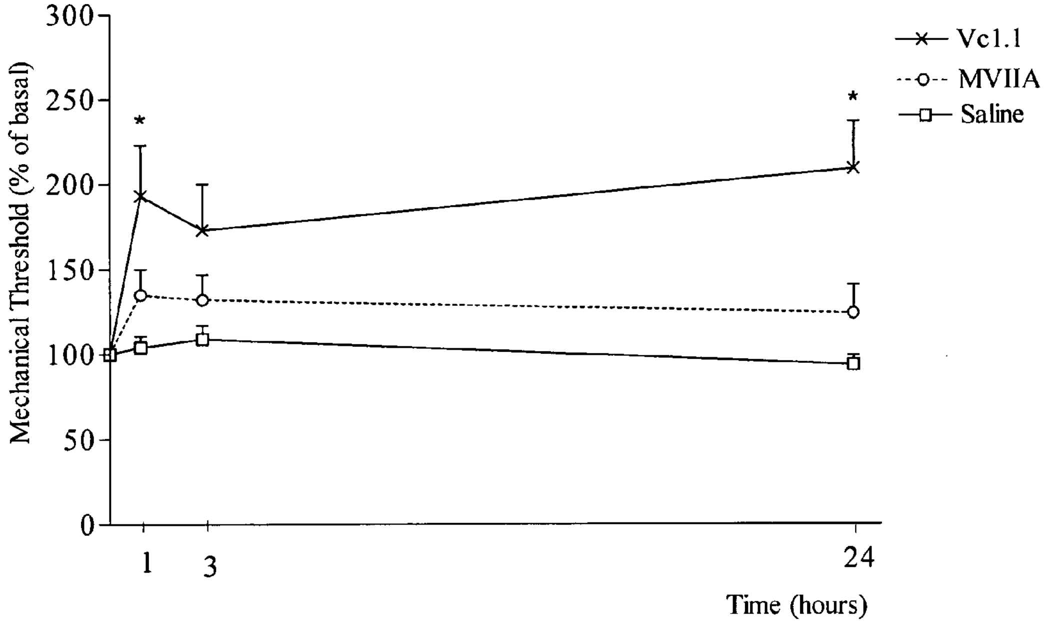
FIG. 6*a* illustrates the short-term effect of intramuscular injection of saline, 0.53 μg/200 μL ω-conotoxin MVIIA or 0.36 μg/200 μL α-conotoxin Vc1.1 on mechanical pain threshold in rats with chronic constriction injury. Mechanical pain threshold is expressed as percentage of base-line data. Each data point represents the mean±SEM of 6 rats in each group. The asterisks indicate that the threshold for the group which received α-conotoxin Vc1.1 was significantly different from that for the saline control group at 1 hour and 24 hours post injection ($p<0.05$).
Figure 6B:
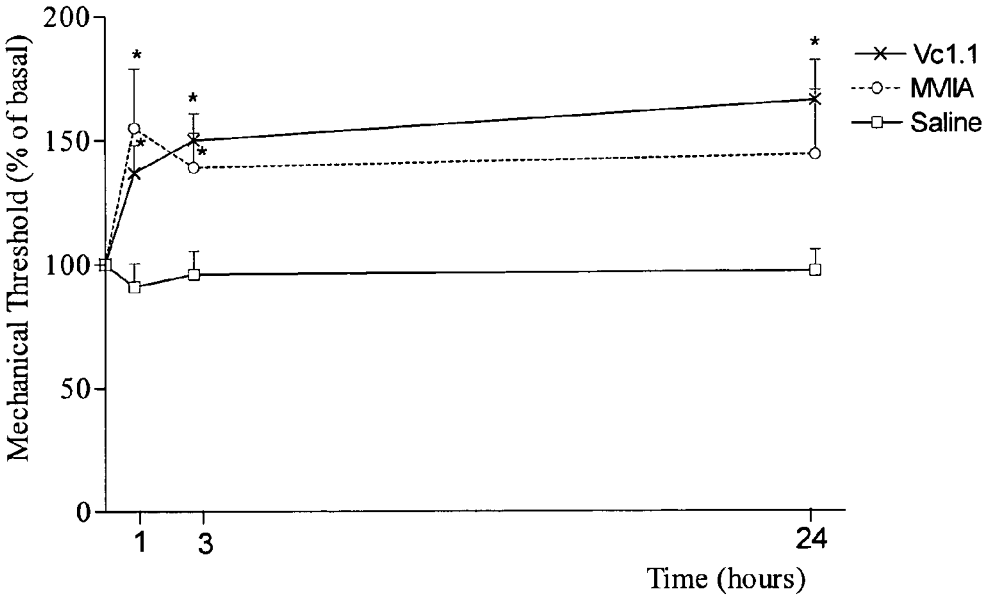
FIG. 6*b* illustrates the short-term effect of subcutaneous injection into the footpad receptive field of injured neurons, of saline, 0.53 μg/2.5 μL ω-conotoxin MVIIA or 0.36 μg/2.5 μL α-conotoxin Vc1.1 on mechanical pain threshold in rats with chronic constriction injury. Mechanical pain threshold is expressed as percentage of base-line data. Each data point represents the mean±SEM of 6 rats in each group. The asterisks indicate that the threshold for the group which received α-conotoxin Vc1.1 was significantly different from that for the saline control group at 1 hour and 24 hours post injection ($p<0.05$).
Figure 7A:
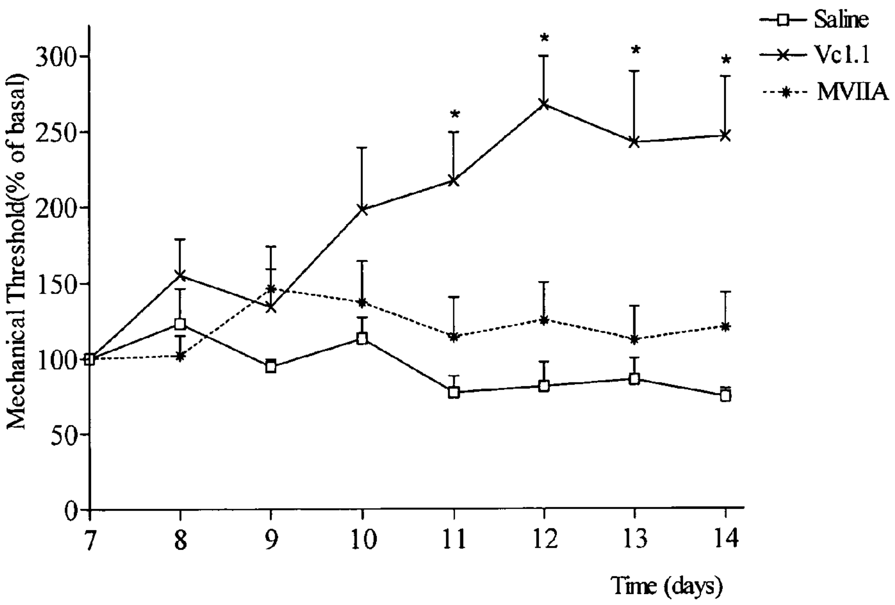
FIG. 7*a* illustrates the effect of daily intramuscular injection of saline or 0.53 μg/200 μL ω-conotoxin MVIIA and 0.36 μg/200 μL α-conotoxin Vc1.1 on mechanical pain threshold in rats with chronic constriction injury. Mechanical pain threshold is expressed as percentage of base-line data. Each data point represents the mean±SEM of 6 rats in each group. The asterisks indicate that the threshold for the treatment group which received α-conotoxin Vc1.1 was significantly different from that for the saline control group on day 11, day 12, day 13 and day 14 ($p<0.05$).
Figure 7B:
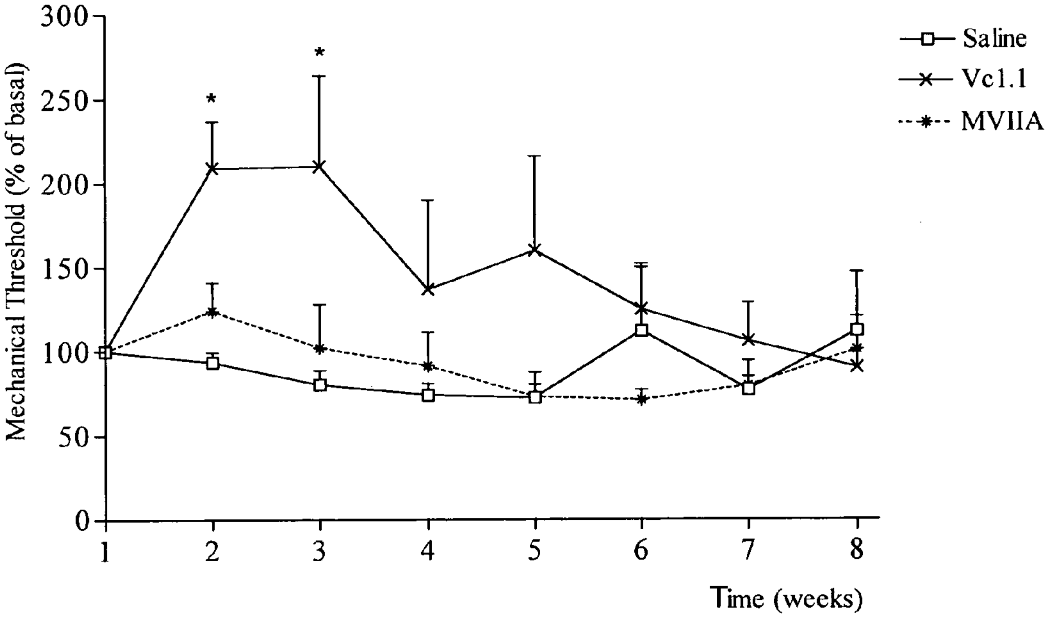
FIG. 7*b* illustrates the long-term effect of intramuscular injection of saline or 0.53 μg/200 μL ω-conotoxin MVIIA or 0.36 μg/200 μL α-conotoxin Vc1.1 on mechanical pain threshold in rats with chronic constriction injury. Intramuscular injections ceased after two weeks. Mechanical pain threshold is expressed as the percentage of base-line data. Each data point represents the mean±SEM of 6 rats in each group. The asterisks indicate that the threshold for the treatment group which received α-conotoxin Vc1.1 was significantly different from that for the control group ($p<0.05$).

Vc1.1 attenuated mechanically-induced hyperalgesia by 89%, 64%, and 116% after 1 hour, 3 hours and 24 hours, respectively, compared to saline-treated controls. These results are summarized in FIGS. 6*a* and *b*. Daily intramuscular injection of Vc1.1 also had significant effects on nerve injury-induced mechanical hyperalgesia at day 11, day 12, day 13 and day 14, corresponding to 140%, 186%, 156% and 172% respectively, as shown in FIG. 7*a*. Vc1.1 was approximately three times more effective than synthetic ω-conotoxin MVIIA at relieving mechanically-induced hyperalgesia over this period of time as shown in FIG. 9*b*. In addition, Vc1.1 attenuated mechanically-induced hyperalgesia for several weeks following cessation of daily intramuscular injections, as shown in FIG. 7*b*.

EXAMPLE 5

Vc1.1 Inhibits Sensory Nerve Function

Figure 8B:
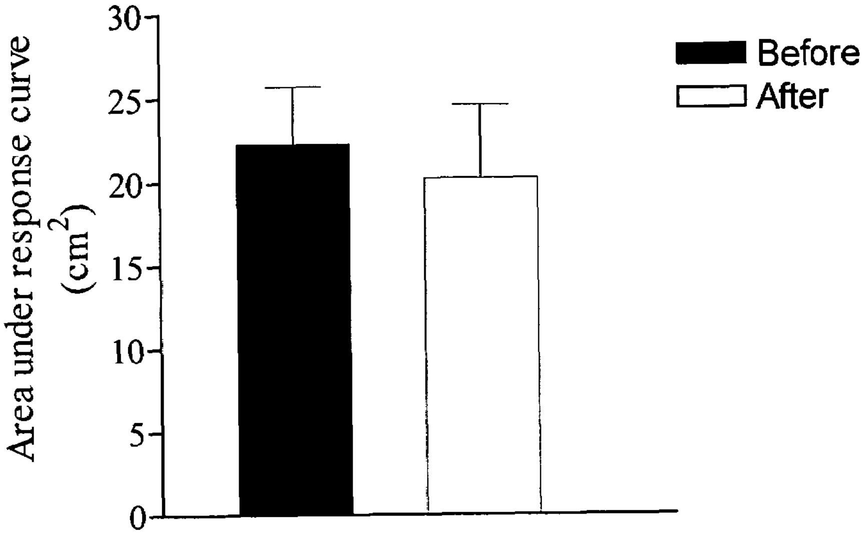

This study compared the effects of three synthetic conotoxins, ω-conotoxin MVIIA, ω-conotoxin GVIA and α-conotoxin Vc1.1, on the vascular response mediated via activation of unmyelinated primary afferent sensory nerves (antidromic stimulation) using low frequency electrical stimulation (LFES) at 20V, 2 ms for 1 min at 5 Hz. The conotoxin peptides were perfused over the base of a blister raised on the footpad of an anaesthetized rat using a suction pressure of −40 kPa. The footpad is innervated by peripheral terminals of the sciatic nerve, and these are accessible to the perfused compounds. Changes in the microvascular blood flow were measured in the skin using laser Doppler flowmetry from the base of the blister (Merhi, Dusting and Khalil, 1998). The three conopeptides were perfused for 30 min prior to electrical stimulation of the sciatic nerve, throughout the 1 min electrical stimulation period and for 20 min following the stimulation. The results illustrated in FIG. 8*a* show that Vc1.1 (1 μM) produced a significant inhibition of the vascular response to low frequency electrical stimulation of the sensory nerves. Changes in the microvascular blood flow are presented as area under the response curve measured in cm2 for 20 min post-stimulation. All three conotoxins tested produced a significant inhibition of the vascular response in response to LFES when compared to the control. There was no significant difference between any of the three conotoxin treatment groups. The degree of inhibition was comparable to that produced by ω-conotoxin GVIA and by ω-conotoxin MVIIA. As the vascular response measured in response to electrical stimulation of sensory nerves not only reflects the ability of these nerves to release neurotransmitters to cause vasodilatation, but also the ability of the smooth muscle cells to dilate, we used sodium nitroprusside (SNP) as an internal control indicator of changes in smooth muscle reactivity. SNP is a direct smooth muscle cell dilator, which acts independently of sensory nerves. SNP was perfused for 10 min. over the blister base in the presence or absence of the conotoxin to see if the action of the conotoxin tested was dependent or independent of an action on smooth muscle reactivity. The SNP (100 μM, dissolved in Ringer's solution) was perfused over the blister base for 10 min followed by a 10 min washout with Ringer's until blood flow was returned to baseline. The results in the absence of Vc1.1 (24.5±1.4) were not significantly different to the results in the presence of Vc1.1 (23.0±1.6) (n=22). The results, shown in FIG. 8*b*, show that perfusion of Vc1.1 did not alter the response to SNP, indicating that the inhibitory effect of Vc1.1 on the vascular response to sensory nerve stimulation is mediated via an action which is independent of changes in smooth muscle reactivity. The most likely explanation is that Vc1.1 inhibits the release of sensory neurotransmitters from the stimulated sensory nerves.

We propose, based on the above results, that the most likely mechanism of action of Vc1.1 is one which involves blocking the neuronal type nicotinic acetylcholine receptors on sensory nerves. This is not to exclude other mechanisms (for example possible blocking of N-type $Ca^{++}$ channels), and indeed appears likely since a functional association of specific presynaptic nAChRs and voltage-gated calcium channels has been demonstrated (Kulak et al, 2001).

EXAMPLE 6

Vc1.1 Accelerates the Rate of Recovery from Nerve Injury

Figure 12A:
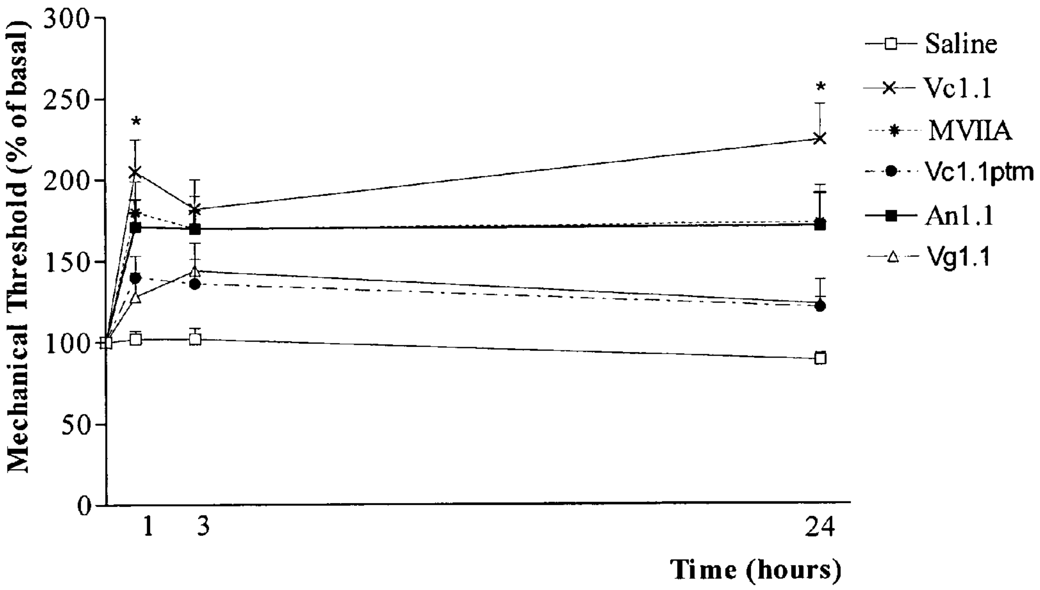
Figure 12B:
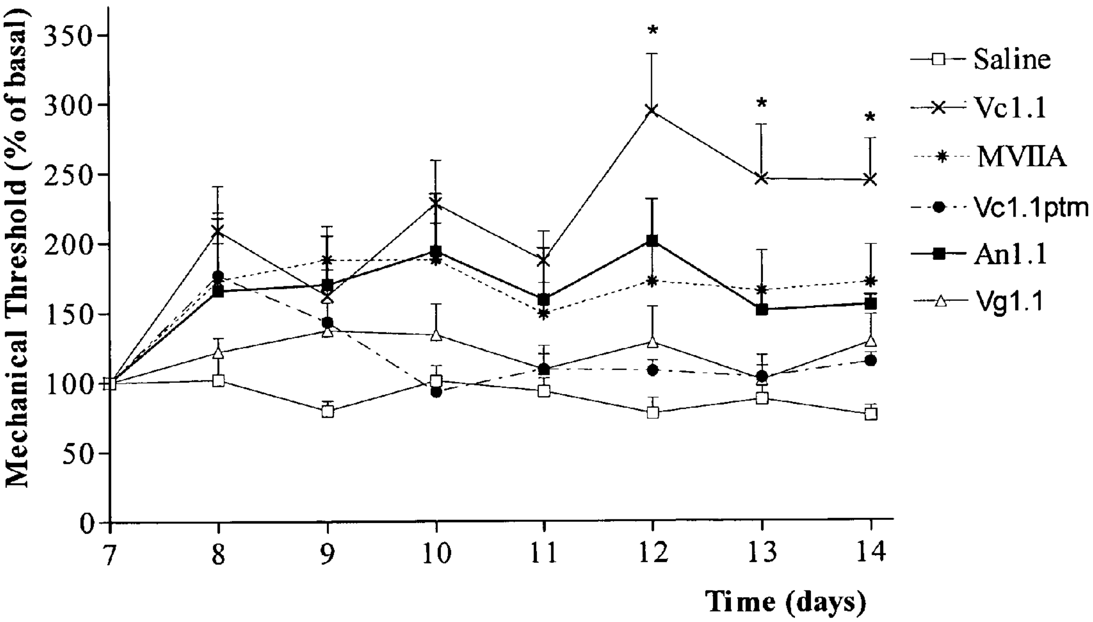
Figure 12C:
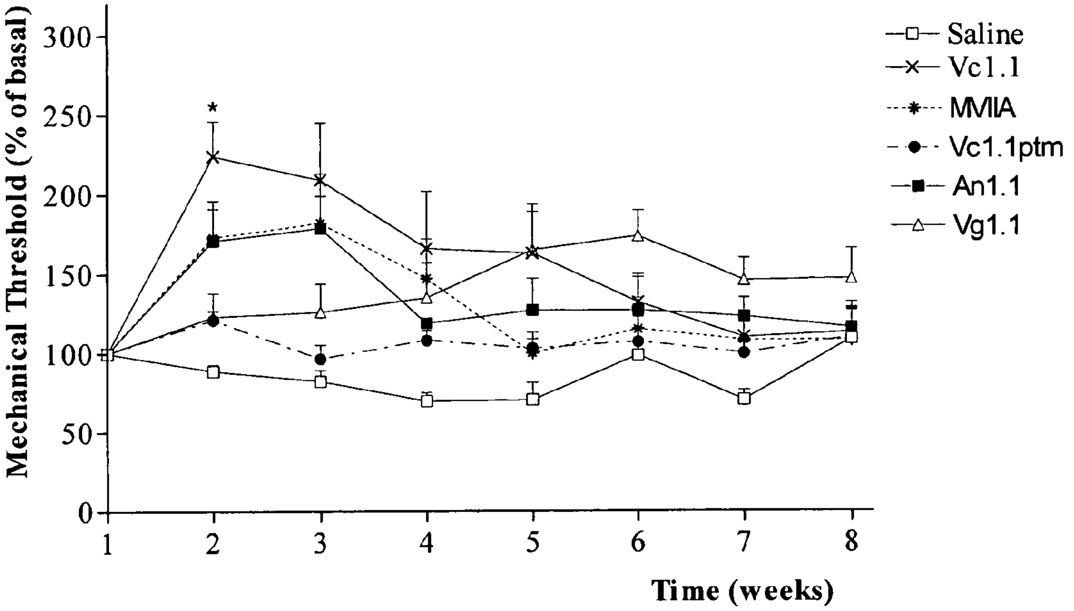
Figure 12D:
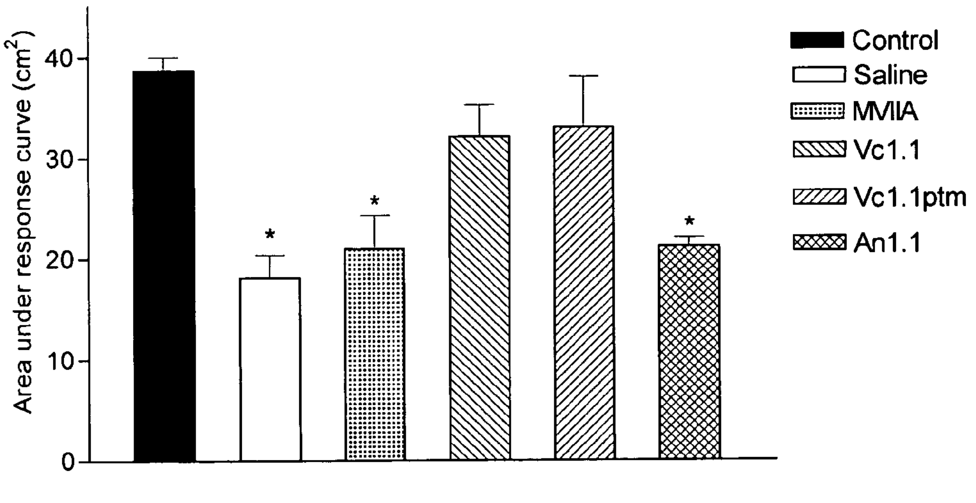

Previous studies in our laboratory (Khalil et al 1999) showed that recovery from chronic constriction nerve injury can be determined by a reduction in hyperalgesia and a return to normal of the peripheral vascular response in an area innervated by the injured nerve. The vascular response can be examined by the perfusion of a vasodilator (substance P, which acts via a preterminal mechanism) over a base of a blister raised over an area innervated by the injured nerve. FIGS. 10*b* and 12*b* show the vascular response to perfusion of substance P at 1 μM after week 8. The Vc1.1 treated group showed 83% and the Vc1.1ptm treated group showed 85% recovery compared to control. The vascular response in both saline (47%) and MVIIA (54%) treated groups remained significantly different from the control, suggesting incomplete functional recovery. The sciatic nerve includes sensory, sympathetic and motor nerves; however this particular vascular test specifically reflects the function of sensory components of the nerve as substance P induces a vasodilator effect via a sensory-dependent mechanism. Therefore, a return of this vascular response to normal reflects functional recovery of sensory nerves demonstrated by their ability to mount an inflammatory vascular response. The results show that both Vc1.1 and Vc1.1ptm were effective in returning the vascular response to normal after 8 weeks.

EXAMPLE 7

Isolation of Peptide Vg1.1

Peptide Vg1.1 was isolated from the venom ducts of *Conus Virgo* (collected at Lizard Island, North Queensland) by the same molecular approach as described for the isolation of Vc1.1 from *Conus victoriae* (see Example 1 above). Clones were selected, and the nucleotide sequence of the clone encoding Vg1.1 was amplified using RTPCR/RACE technology. The amino acid sequence for Vg1.1 was deduced and synthesized commercially (AusPep, Melbourne) by solid-phase peptide synthesis, and the disulfide bonds allowed to form by air oxidation. The deduced peptide Vg1.1 has the structure:

D C C S N P P C A H N N P D C-$NH_2$ (SEQ ID NO:8)

in which the C-terminus cysteine is amidated.

The synthesized peptide was tested as described for Vc1.1 for its ability to (1) inhibit the neuronal-type nicotinic acetylcholine receptor response in bovine adrenal medullary chromaffin cells in culture, (2) compete functionally for the nicotinic response of chromaffin cells (release of adrenaline and noradrenaline) and (3) inbibit the vascular response to electrical stimulation of the sciatic nerve in a rat and to prevent pain in the CCI model of neuropathic pain in the rat.

The results are shown in FIGS. 12 and 13.

EXAMPLE 8

Isolation of Peptide An1.1

Peptide An1.1 was isolated as described above for Vg1.1, except that the source of the peptide was the venom ducts of *Conus anemone* collected from Edithburgh, St Vincent's Gulf, South Australia). The deduced structure of peptide An1.1 is:

G C C S H P A C Y A N N Q D Y C-$NH_2$ (SEQ ID NO:9)

In which the C-terminus cysteine is amidated.

The deduced sequence was chemically synthesised commercially (AusPep, Melbourne) and air oxidized. The synthetic peptide was tested in vitro and in vivo as described for Vc1.1. The results are shown in FIGS. 12 and 14.

The sequences of Vc1.1, Vc1.1ptm, An1.1 and Vg1.1 can be aligned as follows, to illustrate the high degree of homology:

G C C S D P R C N Y D H P E I C-$NH_2$
Vc1.1

G C C S D O R C N Y D H P γ I C-$NH_2$
Vc1.1ptm

G C C S H P A C Y A N N Q D Y C-$NH_2$
An1.1

D C C S N P P C A H N N P D C-$NH_2$
Vg1.1

γ=γ-carboxyglutamate

O=4-Hyp

EXAMPLE 9

Vc1.1 Does Not Affect Blood Pressure

In a preliminary experiment to determine whether the novel α-conotoxins had any adverse systemic side-effects, the effect of Vc1.1 (1 μM in 200 μl im) on resting systolic blood pressure in the rat was measured. FIG. 15 shows that Vc1.1 has no effect upon systemic blood pressure, ie. Vc1.1 does not have a systemic circulatory effect.

DISCUSSION

The association of nicotinic receptor function with pain is relatively new. Earlier work had established that strong nicotinic agonists were analgesics, but the case is not so obvious or well established for nicotinic antagonists. Mice lacking a particular nicotinic receptor subunit in the brain, have reduced pain responses (Marubio et al 1999).

There is now good evidence that nAChRs are also expressed on the somata of cultured sensory dorsal root ganglion (DRG) neurons (Genzen et al 2001), and it is possible that nAChRs are also expressed on the terminals of DRG afferents. The spinal cord contains a subpopulation of inhibitory cholinergic interneurons which make presynaptic contact on to the terminals of primary afferents in the dorsal horn (reviewed by Genzen et al 2001). Acetylcholine in the spinal cord might therefore activate nAChRs expressed on the central terminals of DRG afferents. The sources of acetylcholine which could activate nAChRs on peripheral nerve terminals have not been identified, although there is evidence that many non-neuronal cells either contain or can manufacture acetylcholine (Wessler et al 1999). In addition, Changeux and colleagues have recently shown that up to 40% of neuronal nAChRs are constitutively active, and do not require ACh for activation (Changeux and Edelstein 2001).

Nicotinic antagonists are effective in dampening down the constitutive level of activity. This population of constitutively active receptors may be differentially expressed in higher numbers in a neuroma following peripheral nerve damage. In addition, nicotinic receptor desensitization, which is responsible for the analgesic effects of strong nicotinic agonists such as epibatidine and ABT-594, occurs at much lower agonist concentrations than those needed for nicotinic receptor activation (see Genzen et al 2001), and may play an important role in modulating sensory activity. Others have reported irrative and autonomic responses or hyperalgesia when such agonists are administered at subanalgesic doses (Masner, 1972; Khan et al 1994).

While peripheral applications of nicotinic agonists can cause the excitatory effects described above, behavioural experiments have demonstrated that nicotinic agonists can also have analgesic properties. Interestingly, epibatidine bears a resemblance to nicotine. Taking note of the similar structure of epibatidine, but aware that it was too toxic for human use, Daly and his colleagues in association with Abbott Laboratories began to create nicotine-like chemicals hoping that one may be effective as a painkiller (for review see Plotkin, 2000). Of the hundreds of molecules devised and tested, one stood out: ABT-594. Not only did it lack the toxicity of epibatidine, but proved effective against several types of pain, including pain caused by nerve damage against which even opiates are relatively ineffective. Unlike opiates, ABT-594 appears to be non-addictive, enhances alertness rather than causing sedation and has relatively little effect upon the respiratory system. It lacks the major side effects of morphine, such as constipation and addiction, but has yet to receive regulatory approval.

ABT-594, like epibatidine, is an nicotinic agonist with analgesic potency greater than morphine, and can produce analgesia when administered systemically, intradermally or centrally in the nucleus raphe magnus, a site involved in descending modulatory system of analgesia.

Whereas the excitatory effects of nicotinic agonists are primarily due to nAChR activation with subsequent neuronal depolarization leading to $Na^+$ or $Ca^{2+}$ channel activation, we propose that the inhibitory effects of strong nicotinic agonists like epibatidine and derivatives such as ABT-594, may be due to receptor desensitization and $Na^+$ or $Ca^{2+}$ channel closure. This has not been suggested previously, and indicated that nicotinic antagonists, such as the α-conotoxins are useful as analgesics for clinical use against pain.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Albuquerque E X, Alkondon M, Pereira E F, Castro N G, Schrattenholz A, Barbosa C T, Bonfante-Cabarcas R, Aracava Y, Eisenberg H M, Maelicke A (1997) Properties of neuronal nicotinic acetylcholine receptors: pharmacological characterization and modulation of synaptic function. J. Pharmacol. Exp. Ther. 280 1117-1136

Aubert I, Arujo D M, Cecyre D, Robitaille Y, Gauthier S, Quirion R (1992) Comparative alterations of nicotinic and muscarinic sites in Alzheimer's and Parkinson's diseases. Journal of Neurochemistry 58, 529-541.

Bandyopadhyay P K, Garrett J E, Shetty R P, Keate T, Walker C S, Olivera B M. (2002) From the Cover: gamma-Glutamyl carboxylation: An extracellular post-translational modification that antedates the divergence of molluscs, arthropods, and chordates. Proc Natl Acad Sci U S A. 99:1264-1269.

Baneyx F. (1999) Recombinant protein expression in *Escherichia coli*. Current Opinion in Biotechnology, 10: 411-421

Bennett G J and Xie Y K (1988) A peripheral mononeuropathy in rat that produces disorder of pain sensation like those seen in man. Pain 33, 87-107.

Bingham J P, Jones A, Lewis R J, Andrews, PR, Alewood, PF (1996) *Conus* venom peptides (conopeptides): interspecies, intraspecies and within individual variation revealed by ionspray mass spectroscopy. In Lazarovici P, Spira M E, Zlotkin, E, Biochemical Aspects of Marine Pharmacology. Alaken Inc. Fort Collins, Colo., 13-27.

Bowersox S, Mandema J, Tarczy-Hornoch K, Miljanich G, Luther R R (1997) Pharmacokinetics of SNX-111, a selective N-type calcium channel blocker, in rats and cynomolgus monkeys.

Drug Metab Dispos. 25, 379-83.

Bowersox S S, Singh T, Luther R R (1996) Selective N-type neuronal voltage-sensitive calcium channel blocker, SNX-111, produces spinal antinociception in rat models of acute, persistent and neuropathic pain. Journal of Pharmacological Experimental Therapeutics 279, 1243-1249.

Broxton N, Miranda L, Gehrmann J, Down J, Alewood P. and Livett B (2000) $Leu^{10}$ of α-conotoxin PnIB confers potency for neuronal nicotinic responses in bovine chromaffin cells. Europ. J. Pharmacol. 390: 229-236.

Campos-Caro A, Smillie F I, Dominguez del Toro E, Rovira J C, Vicente-Agullo F, Chapuli J, Juiz J M, Sala S, Sala F, Ballesta J J, Criado M (1997) Neuronal nicotinic acetylcholine receptors on bovine chromaffin cells: cloning, expression and genomic organization of receptor subunits. Journal of Neurochemistry 68, 488-497.

Castanié M P, Bergès H, Oreglia J, Prère M F, Fayet O (1997) A set of pBR322-compatible plasmids allowing the testing of chaperone assisted folding of proteins overexpressed in *Escherichia coli*. Anal Biochem, 254: 150-152.

Changeux J, Edelstein S J (2001) Allosteric mechanisms in normal and pathological nicotinic acetylcholine receptors. Curr Opin Neurobiol. 11:369-77. [REVIEW]

Chorev M and Goodman M (1993) A dozen years of retro-inverso peptidomimetics. Acc. Chem. Res. 26 266-273

Codignola A, McIntosh J M, Cattaneo M G, Vicentini L M, Clementi F, Sher E. (1996) alpha-Conotoxin imperialis I inhibits nicotine-evoked hormone release and cell proliferation in human neuroendocrine carcinoma cells. Neurosci Lett. 206:53-56

Decker, MW, Meyer, MD, Sullivan, JP (2001) The therapeutic potential of nicotinic acetylcholine receptor agonists for pain control. Expert Opin Investig Drugs. 2001 Oct; 10 (10):1819-30. Review Favreau P, Krimm I, Le Gall F, Bobenrieth M J, Lamthanh H, Bouet F, Servent D, Molgo J, Menez A, Letourneux Y, Lancelin J M (1999) Biochemical characterization and nuclear magnetic resonance structure of novel alpha-conotoxins isolated from the venom of *Conus* consors. Biochemistry 38 (19) 6317-26.

Freidinger R M, Perlow D S, Veber D F (1982) Protected lactam-bridged dipeptides for use as conformational constraints in peptides, *J. Org. Chem.* 47, 104-109

Gallop M A, Barrett R W, Dower W J, Fodor S P, Gordon E M (1994) Applications of combinatorial technologies to drug discovery. 1. Background and peptide combinatorial libraries. J Med. Chem. 1994 37, 1233-1251. [Review]

Genzen, J. R., Cleve, W. V. and McGhehee D. S. (2001) Dorsal root ganglion neurons express multiple nicotinic acetylcholine receptor subtypes. J. Neurophysiol. 86: 1773-1782.

Gerzanich V, Peng X, Wang F, Wells G, Anand R, Fletcher S, and Lindstrom J. (1995) Comparative pharmacology of epibatidine: a potent agonist for neuronal nicotinic acetylcholine receptors. Mol. Pharmacol 48: 774-782.

Guan Z Z, Zhang X, Ravid R, Nordberg A (2000) Decreased protein levels of nicotinic receptor subunits in the hippocampus and temporal cortex of patients with Alzheimer's disease. Journal of Neurochemistry 74, 237-243.

Groebe D R, Gray W R, Abramson S N (1997) Determinants involved in the affinity of alpha-conotoxins GI and SI for the muscle subtype of nicotinic acetylcholine receptors. Biochemistry 36, 6469-6474.

Heading C (1999) "Ziconotide, Neurex Corp". Current Opinion in CPNS Investigational Drugs 1, 153-166. [Review].

Hottenrott S, Schumann T, Plückthun A, Fischer G, Rahfeld J-U (1997) The *Escherichia coli* SlyD is a metal ion-regulated peptidyl-prolyl cis/trans isomerase. J Biol Chem, 272:15697-15701.

Hogan J C (1997) Combinatorial chemistry in drug discovery. Nature Biotechnology, 15 328-330.

Jain, K K (2000) An evaluation of intrathecal ziconotide for the treatment of chronic pain. Expert Opin Investig Drugs. 9, 2403-10. [Review].

Hogg R C, Miranda L P, Craik D J, Lewis R J, Alewood P F and Adams D J (1999) Single amino acid substitutions in alpha-Conotoxin PnIA shift selectivity for subtypes of the mammalian neuronal nicotinic acetylcholine receptor. J. Biol. Chem. 274: 36559-36564.

Jones A, Bingham J P, Gehrmann J, Bond T, Loughnan M, Atkins A, Lewis R J and Alewood P F (1996) Isolation and characterization of conopeptides by high-performance liquid chromatography combined with mass spectrometry and tandem mass spectrometry. Rapid Commun. Mass Spectrom. 10, 138-143.

Jones R M, Bulaj G (2000) Conotoxins—new vistas for peptide therapeutics. Curr Pharm Des. 6, 1249-85. [Review].

Karlin, A. (2002) Emerging structure of the nicotinic acetylcholine receptors. Nat Rev Neurosci 3: 102-114. [Review].

Khalil, Z, Liu, T. and Helme, R.D. (1999) Free radicals contribute to the reduction in neurogenic vascular responses and maintenance of thermal hyperalgesia in rats with chronic constriction injury. Pain: 79: 31-37.

Khan I M, Taylor P and, Yaksh T L (1994) Stimulatory pathways and sites of action of intrathecally administered nicotinic agents. J. Pharmcol. Exp. Ther. 271: 1550-1557.

Kulak J M, McIntosh, J M, Yoshikami D, and Olivera B M (2001) Nicotine-evoked transmitter release in synaptosomes: functional association of specific presynaptic acetylcholine receptors and voltage-gated calcium channels. J. Neurochem. 77:2581-89.

Lewis R J, Bingham J P, Jones A, Alewood P F, Andrews P R (1994) Drugs from the peptide venoms of marine cone shells.

Australia's Biotechnol. 4, 298-300. [Review].

Lin, S-R, Chang L S, Chang, CC (1999) Disufide isomers of α-neurotoxins from King Cobra (*Ophiophagus hannah*) Venom; Biochem. & Biophys. Res. Commun. 254, 104-108

Livett B G, Mitchelhill K I, Dean D M (1987a) Adrenal chromaffin cells—their isolation and culture. In Poisner A M, Trifaro J M (eds) The Secretory Process, Vol 3. In-vitro methods for studying secretion. Elsevier, Amsterdam, 171-175.

Livett B G, Marley P D, Mitchelhill K I, Wan D C, White T D (1987b) Assessment of adrenal chromaffin cell secretion: Presentation of four techniques. In Poisner A M and Trifaro J M (eds) The Secretory Process, Vol 3, In vitro methods for studying secretion. Elsevier, Amsterdam, 177-204.

Loughnan M, Bond T, Atkins A, Cuevas J, Adams D J, Broxton N M, Livett B G, Down J G, Jones A, Alewood P F, Lewis R J (1998) alpha-conotoxin EpI, a novel sulfated peptide from *Conus episcopatus* that selectively targets neuronal nicotinic acetylcholine receptors. Journal of Biological Chemistry 273, 15667-15674.

Lukas R J, Changeux J P, Le Novere N, Albuquerque E X, Balfour D J, Berg D K, Bertrand D, Chiappinelli V A, Clarke P B, Collins A C, Dani J A, Grady S R, Kellar K J, Lindstrom J M, Marks M J, Quik M, Taylor P W, Wonnacott S. (1999) International Union of Pharmacology. XX. Current status of the nomenclature for nicotinic acetylcholine receptors and their subunits. Pharmacol Rev. 51, 397-401. [Review].

Luo S, Kulak J M, Cartier G E, Jacobsen R B, Yoshikami D, Olivera B M and McIntosh J M (1998). alpha-conotoxin AuIB selectively blocks alpha3 beta4 nicotinic acetylcholine receptors and nicotine-evoked norepinephrine release. J Neurosci 18:8571-8579

Maillo, M., M. B. Aguilar, E. Lopez-Vera, A. G. Craig, G. Bulaj, B. M. Olivera and E. P. Heimer de la Cortera (2001) Conorfamide, a *Conus* venom peptide belonging to the RFamide family of neuropeptides. Toxicon, 40:401-407.

Marubio L M, Arroyo-Jimenez M D M, Cordero-Erausquin M, Lena C, LeNovere N, DExaerde A K, Hucket M, Damaj M I and Changeux J P (1999). Reduced antinociception in mice lacking neuronal nicotinic receptor subunits. Nature 398, 805-810.

Masner R (1972) Relation between some central effects of nicotine and its brain levels in the mouse. Ann. Med. Exp. Biol. Fenniae 50: 205-212

McIntosh J M, Yoshikami D, Mahe E, Nielsen D B, Rivier J E, Gray W R, Olivera B M. (1994) A nicotinic acetylcholine receptor ligand of unique specificity, alpha-conotoxin Iml. J. Biol. Chem. 269:16733-16739.

McIntosh J M and Jones R M (2001) Cone venom—from accidental stings to deliberate injection. Toxicon 39: 1447-1451.

McIntosh J M, Santos A D, Olivera B M (1999) *Conus* peptides targeted to specific nicotinic acetylcholine receptor subtypes. Annual Review of Biochemistry 68, 59-88.

McIntosh J M, Corpuz G O, Layer R T, Garrett J E, Wagstaff J D, Bulaj G, Vyazovkina A, Yoshikami D, Cruz L J, Olivera B M. (2000) Isolation and characterization of a novel *conus* peptide with apparent antinociceptive activity. J Biol. Chem. 2000 Oct. 20; 275(42):32391-7.

Merhi, M., Dusting, G. J. and Khalil, Z. (1998) CGRP and nitric oxide of neuronal origin mediate neurogenic vasodilatation in rat skin microvasculature. Br. J. Pharmacol. 123:863-868.

Miranda, L P and Alewood, P F. (1999) Accelerated chemical synthesis of peptides and small proteins. Proc Natl Acad Sci USA. 96:1181-1186.

Mukherjee S, Mahadik S P, Korenovsky A, Laev H, Schnur D B, Reddy R (1994) Serum antibodies to nicotinic acetylcholine receptors in schizophrenic patients. Schizophrenia Research 12, 131-136.

Nagai U, Sato K (1985) Synthesis of a bicyclic dipeptide with the shape of β-turn central part. Tetrahedron Lett. 26, 647-650.

Nishihara K, Kanemori M, Kitagawa M, Yanaga H, Yura T (1998) Chaperone-coexpression plasmids: differential and synergistic roles of DnaKDnaJ-GrpE and GroEL-GroES in assisting folding of an allergen of Japanese cedar pollen, Cryj2, in *Escherichia coli*. Appl Environ Microbiol, 64:1694-1699.

Olivera B M, Rivier J, Clark C, Ramilo C A, Corpuz G P, Abogadie F C, Mena E E, Woodward S R, Hillyard D R, Cruz L J (1990) Diversity of *Conus* neuropeptides. Science 249, 257-263.

Olivera, B. M. and L. J. Cruz (2001) Conotoxins, in retrospect. Toxicon 39:7-14.

Olson G L, Bolin D R, Bonner M P, Bos M, Cook C M, Fry D C, Graves B J, Hatada M, Hill D E, Kahn M. et al (1993) Concepts and progress in the development of peptide mimetics [Review] J. Medicinal Chem., 36 3039-3049.

Penn R D, Paice J A (2000) Adverse effects associated with the intrathecal administration of ziconotide. Pain. 85 (1-2):291-296.

Plotkin, MJ (2000) Chapter 1 in: "Medicine Quest" by Mark J. Plotkin, Viking-Penguin Group.

Price-Carter M, Bulaj G, Goldenberg D P. (2002) Initial Disulfide Formation Steps in the Folding of an omega-Conotoxin. Biochemistry. 41:3507-3519.

Qiu J, Swartz J R, Georgiou G (1998) Expression of active human tissue type plasminogen activator in *Escherichia coli*. Appl Environ Microbiol 1998, 64:4891-4896.

Randall A, and Selitto J J (1957). A method for measurement of analgesic activity on inflamed tissue. Arch. Int. Pharmacodyn. Ther. 111: 409-419.

Sargent P B (1993) The diversity of neuronal nicotinic acetylcholine receptors. Annual Review of Neuroscience 16, 403-443.

Screenivasan, A (2002) Keeping up with the cones: chased by evolutionary biologists and pharmacological researchers, a tropical mollusk redefines "a snail's pace". Natural History, 111, 40-48. [Review]

Shen G S, Layer R T, McCabe R T (2000) Conopeptides: From deadly venoms to novel therapeutics. Drug Discovery Today 5, 98-106.

Smythe M L, von Itzstein M (1994) Design and synthesis of a biologically active antibody mimic based on an antibody-antigen crystal structure. J. Am. Chem. Soc. 116, 2725-2733.

Steinlein O K, Mulley J C, Propping P, Wallace R H, Phillips H A, Sutherland G R, Scheffer I E, Berkovic S F (1995) A missense mutation in the neuronal nicotinic acetylcholine receptor alpha subunit is associated with autosomal dominant nocturnal frontal lobe epilepsy. Nature Genetics 11, 201-203.

Stoller G, Rücknagel K P, Nierhaus K H, Schmid F X, Fischer G. Rahfeld J-U (1995) A ribosome-associated peptidyl-prolyl cis/trans isomerase associated as the trigger factor. EMBO J, 14:4939-4948.

Thomas J G, Baneyx F (1996) Protein misfolding and inclusion body formation in recombinant *Escherichia coli* cells overproducing heat-shock proteins. J Biol Chem, 271:11141-11147.

Wessler, I Kirkpatrick, C. J. and Racke, K. (1999) The cholinergic 'pitfall': acetylcholine, a universal cell molecule in biological systems, including humans. Clin. Exp. Pharmacol. Physiol.26: 198-205. [Review]

Wonnacott S (1997) Presynaptic nicotinic ACh receptors. Trends in Neuroscience 20, 92-98.

Zhao Q, Smith M L, Siesjo B K (1994) The omega-conopeptide SNX-111, an N-type calcium channel blocker, dramatically ameliorates brain damage due to transient focal ischaemia. Acta Physiol Scand. 150, 459-61.

The invention claimed is:

1. An isolated α-conotoxin-like peptide up to 19 amino acid residues in length, comprising the following sequence of amino acids:

(SEQ ID NO:12)
$Xaa_1$-Cys-Cys-Ser-$Xaa_2$-$Xaa_3$-$Xaa_4$-Cys-$Xaa_5$-$Xaa_6$-$Xaa_7$-$Xaa_8$-$Xaa_9$-$Xaa_{10}$-$Xaa_{11}$-Cys, wherein:

$Xaa_1$ is Gly or Asp;
$Xaa_2$ is Asp, His or Asn;
$Xaa_3$ is Pro, hydroxyproline or Gln;
$Xaa_4$ is Ala, Pro or Arg;
$Xaa_5$ is Asn, Ala or Tyr;
$Xaa_6$ is Ala, Tyr or His
$Xaa_7$ is Asn or Asp;
$Xaa_8$ is His or Asn;
$Xaa_9$ is Pro, hydroxyproline or Gln;
$Xaa_{10}$ is Asp, Glu or γ-carboxyglutamate;
$Xaa_{11}$ is Ile or Tyr; and
the C-terminus is optionally amidated.

2. An isolated peptide according to claim 1 in which the C-terminus is amidated.

3. An isolated peptide according to claim 1, comprising the following sequence of amino acids:

(SEQ ID NO: 1)
Gly-Cys-Cys-Ser-Asp-$Xaa_1$-Arg-Cys-Asn-Tyr-Asp-His-$Xaa_2$-$Xaa_3$-Ile-Cys in which $Xaa_1$ is Pro or hydroxyproline;
$Xaa_2$ is Pro, hydroxyproline or Gln;
$Xaa_3$ is Asp, Glu or γ-carboxyglutamate;
and the C-terminus is optionally amidated.

4. An isolated peptide according to claim 1, which acts as an analgesic in mammals.

5. An isolated peptide according to claim 1, which comprises a sequence selected from the group consisting of:

(SEQ ID NO: 2)
(i) Gly-Cys-Cys-Ser-Asp-Pro-Arg-Cys-Asn-Tyr-Asp-His-Pro-Glu-Ile-Cys-$NH_2$ (SEQ ID NO:7)
(ii) Gly-Cys-Cys-Ser-Asp-4Hyp-Arg-Cys-Asn-Tyr-Asp-His-Pro-γ-carboxy-Glu-Ile-Cys-$NH_2$.

6. An isolated peptide according to claim 5, which comprises the amino acid sequence of SEQ ID NO:2.

7. An isolated peptide according to claim 5, which comprises the amino acid sequence of SEQ ID NO:7.

8. An isolated peptide according to claim 1, which induces analgesia.

9. A peptide according to claim 8 which has 16 amino acid residues in a 4:7 loop framework, in which the Cys residues are bonded via disulfide bonds as follows, counting the Cys residues from the N-terminus:

(i) the first Cys is bonded to the third Cys and
(ii) second Cys bonded to the fourth Cys.

10. A composition comprising a peptide according to claim 1, together with a physiologically acceptable carrier.

11. An isolated peptide according to claim 1 wherein $Xaa_1$ is Gly or Asp,
$Xaa_2$ is Asp,
$Xaa_3$ is Pro or Hydroxyproline,
$Xaa_4$ is Arg,
$Xaa_5$ is Asn,
$Xaa_6$ is Tyr,
$Xaa_7$ is Asp,
$Xaa_8$ is His,
$Xaa_9$ is Pro or Hydroxyproline,
$Xaa_{10}$ is Asp, Glu or γ-carboxyglutamate, and
$Xaa_{11}$ is Ile.

12. A method for treating pain in a mammalian subject in need thereof comprising the step of administering to said subject a pain-inhibitory effective amount of a peptide according to claim 1 thereby treating said pain.

13. A method according to claim 12 in which the pain is a neurogenic and/or neuropathic pain.

14. A method according to claim 12, in which the pain is cancer pain, post-surgical pain, oral or dental pain, pain from referred trigeminal neuralgia, pain from post-herpetic neuralgia, phantom limb pain, pain from fibromyalgia, or pain due to reflex sympathetic dystrophy.

15. A method according to claim 12, in which the pain is associated with an inflammatory condition.

16. A method according to claim 15 wherein the inflammatory condition is associated with rheumatoid arthritis, another type of inflammatory arthritis or degenerative arthritis.

* * * * *

SEQUENCE LISTING

```
<160> NUMBER OF SEQ ID NOS: 9

<210> SEQ ID NO 1
<211> LENGTH: 16
<212> TYPE: PRT
<213> ORGANISM: Conus sp.
<220> FEATURE:
<221> NAME/KEY: MISC_FEATURE
<222> LOCATION: (6)..(6)
<223> OTHER INFORMATION: Xaa is proline or hydroxyproline
<220> FEATURE:
<221> NAME/KEY: MISC_FEATURE
<222> LOCATION: (13)..(13)
<223> OTHER INFORMATION: Xaa is proline, hydroxyproline or glutamine
<220> FEATURE:
<221> NAME/KEY: MISC_FEATURE
<222> LOCATION: (14)..(14)
<223> OTHER INFORMATION: Xaa is aspartate, glutamate or gamma-
      carboxyglutamate

<400> SEQUENCE: 1

Gly Cys Cys Ser Asp Xaa Arg Cys Asn Tyr Asp His Xaa Xaa Ile Cys
1               5                   10                  15


<210> SEQ ID NO 2
<211> LENGTH: 16
<212> TYPE: PRT
<213> ORGANISM: Conus victoriae
<220> FEATURE:
<221> NAME/KEY: MOD_RES
<222> LOCATION: (16)..(16)
<223> OTHER INFORMATION: AMIDATION

<400> SEQUENCE: 2

Gly Cys Cys Ser Asp Pro Arg Cys Asn Tyr Asp His Pro Glu Ile Cys
1               5                   10                  15


<210> SEQ ID NO 3
<211> LENGTH: 270
<212> TYPE: DNA
<213> ORGANISM: Conus victoriae

<400> SEQUENCE: 3

atgggcatgc ggatgatgtt caccgtgttt ctgttggttg tcttggcaac cactgtcgtt      60

tcctccactt caggtcgtcg tgaatttcgt ggcaggaatg ccgcagccaa agcgtctgac     120

ctggtcagtt tgaccgacaa gaagcgagga tgctgtagtg atcctcgctg taactatgat     180

catccagaaa tttgtggttg aagacgctga tgctccacga ccctctgaac cacgacacgc     240

cgccctctgc ctgacctgct tcactttccg                                      270


<210> SEQ ID NO 4
<211> LENGTH: 66
<212> TYPE: PRT
<213> ORGANISM: Conus victoriae

<400> SEQUENCE: 4

Met Gly Met Arg Met Met Phe Thr Val Phe Leu Leu Val Val Leu Ala
1               5                   10                  15

Thr Thr Val Val Ser Ser Thr Ser Gly Arg Arg Glu Phe Arg Gly Arg
            20                  25                  30

Asn Ala Ala Ala Lys Ala Ser Asp Leu Val Ser Leu Thr Asp Lys Lys
        35                  40                  45

Arg Gly Cys Cys Ser Asp Pro Arg Cys Asn Tyr Asp His Pro Glu Ile
```

-continued

```
                 50                  55                  60

Cys Gly
65


<210> SEQ ID NO 5
<211> LENGTH: 20
<212> TYPE: DNA
<213> ORGANISM: artificial sequence
<220> FEATURE:
<223> OTHER INFORMATION: Synthetic nucleotide - probe

<400> SEQUENCE: 5

atgggcatgc ggatgatgtt                                                    20


<210> SEQ ID NO 6
<211> LENGTH: 20
<212> TYPE: DNA
<213> ORGANISM: artificial sequence
<220> FEATURE:
<223> OTHER INFORMATION: Synthetic nucleotide - probe

<400> SEQUENCE: 6

cggaaagtga agcaggtcag                                                    20


<210> SEQ ID NO 7
<211> LENGTH: 16
<212> TYPE: PRT
<213> ORGANISM: Conus victoriae
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (16)..(16)
<223> OTHER INFORMATION: AMIDATION
<220> FEATURE:
<221> NAME/KEY: MISC_FEATURE
<222> LOCATION: (14)..(14)
<223> OTHER INFORMATION: gamma-carboxyglutamate

<400> SEQUENCE: 7

Gly Cys Cys Ser Asp Pro Arg Cys Asn Tyr Asp His Pro Xaa Ile Cys
1               5                   10                  15


<210> SEQ ID NO 8
<211> LENGTH: 15
<212> TYPE: PRT
<213> ORGANISM: Conus Virgo
<220> FEATURE:
<221> NAME/KEY: MOD_RES
<222> LOCATION: (15)..(15)
<223> OTHER INFORMATION: AMIDATION

<400> SEQUENCE: 8

Asp Cys Cys Ser Asn Pro Pro Cys Ala His Asn Asn Pro Asp Cys
1               5                   10                  15


<210> SEQ ID NO 9
<211> LENGTH: 16
<212> TYPE: PRT
<213> ORGANISM: Conus anemone
<220> FEATURE:
<221> NAME/KEY: MOD_RES
<222> LOCATION: (16)..(16)
<223> OTHER INFORMATION: AMIDATION

<400> SEQUENCE: 9
```

-continued

```
Gly Cys Cys Ser His Pro Ala Cys Tyr Ala Asn Asn Gln Asp Tyr Cys
1               5                   10                  15
```